United States Patent
Christopher et al.

(10) Patent No.: US 8,015,974 B2
(45) Date of Patent: *Sep. 13, 2011

(54) SYSTEM FOR PROVIDING FLOW-TARGETED VENTILATION SYNCHRONIZED TO A PATIENT'S BREATHING CYCLE

(75) Inventors: Kent L. Christopher, Denver, CO (US); Stephanie S. Diehl, Littleton, CO (US)

(73) Assignee: CS Medical, Inc., Boulder, CO (US)

( * ) Notice: Subject to any disclaimer, the term of this patent is extended or adjusted under 35 U.S.C. 154(b) by 469 days.

This patent is subject to a terminal disclaimer.

(21) Appl. No.: 12/021,641

(22) Filed: Jan. 29, 2008

(65) Prior Publication Data

US 2008/0178882 A1    Jul. 31, 2008

Related U.S. Application Data

(63) Continuation of application No. 11/627,512, filed on Jan. 26, 2007.

(51) Int. Cl.
*A61M 15/08*        (2006.01)
*A61M 16/00*        (2006.01)
*A61M 15/00*        (2006.01)

(52) U.S. Cl. .......... 128/207.18; 128/200.26; 128/200.24
(58) Field of Classification Search ............. 128/200.24, 128/200.26, 204.18, 204.21, 204.23, 207.14, 128/207.18

See application file for complete search history.

(56) References Cited

U.S. PATENT DOCUMENTS

| | | |
|---|---|---|
| 2,735,432 A | 2/1956 | Hudson |
| 2,868,199 A | 1/1959 | Hudson |
| 3,648,703 A | 3/1972 | Manker |
| 3,754,552 A | 8/1973 | King |
| 3,814,103 A | 6/1974 | Fettel et al. |
| 4,273,124 A | 6/1981 | Zimmerman |
| 4,422,456 A | 12/1983 | Tiep |
| 4,480,639 A | 11/1984 | Peterson et al. |
| 4,520,812 A | 6/1985 | Freitag et al. |
| 4,589,409 A | 5/1986 | Chatburn et al. |
| 4,612,928 A | 9/1986 | Tiep et al. |
| 4,681,099 A | 7/1987 | Sato et al. |
| 4,753,233 A | 6/1988 | Grimes |
| 4,776,333 A | 10/1988 | Miyamae |
| 4,821,715 A | 4/1989 | Downing |
| 4,823,788 A | 4/1989 | Smith et al. |
| 4,982,735 A | 1/1991 | Yagata et al. |
| 5,048,515 A | 9/1991 | Sanso |

(Continued)

FOREIGN PATENT DOCUMENTS

WO    2006070366 A2    7/2006

(Continued)

*Primary Examiner* — Justine Yu
*Assistant Examiner* — Annette Dixon
(74) *Attorney, Agent, or Firm* — Dorr, Carson & Birney, P.C.

(57) ABSTRACT

An open system provides breath-synchronized, flow-targeted ventilation to augment respiration by a self-breathing patient. A sensor detects a physical property of a patient's respiratory cycle. A processor monitors the sensor and controls a gas source to deliver oxygen-containing gas through a tube extending into the patient's airway with the flow rate varying over each respiratory cycle in a predetermined non-constant waveform synchronized with the respiratory cycle to augment the patient's spontaneous respiration. Gas is delivered at a flow rate sufficient to significantly mitigate the airway pressure the patient must generate during spontaneous breathing and thereby reduce the patient's work of breathing.

22 Claims, 32 Drawing Sheets

U.S. PATENT DOCUMENTS

| | | | |
|---|---|---|---|
| 5,074,299 A * | 12/1991 | Dietz | 128/204.21 |
| 5,090,408 A | 2/1992 | Spofford et al. | |
| 5,101,820 A | 4/1992 | Christopher | |
| 5,161,525 A | 11/1992 | Kimm et al. | |
| 5,165,397 A * | 11/1992 | Arp | 128/204.21 |
| 5,181,509 A | 1/1993 | Spofford et al. | |
| 5,279,288 A | 1/1994 | Christopher | |
| 5,390,666 A | 2/1995 | Kimm et al. | |
| 5,419,314 A | 5/1995 | Christopher | |
| 5,515,844 A | 5/1996 | Christopher | |
| 5,535,738 A | 7/1996 | Estes et al. | |
| 5,558,086 A | 9/1996 | Smith et al. | |
| 5,606,968 A * | 3/1997 | Mang | 128/207.14 |
| 5,632,269 A | 5/1997 | Zdrojkowski | |
| 5,653,228 A | 8/1997 | Byrd | |
| 5,660,171 A | 8/1997 | Kimm et al. | |
| 5,682,877 A * | 11/1997 | Mondry | 128/204.23 |
| 5,785,051 A | 7/1998 | Lipscher et al. | |
| 5,803,065 A | 9/1998 | Zdrojkowski et al. | |
| 5,937,858 A | 8/1999 | Connell | |
| 5,954,050 A | 9/1999 | Christopher | |
| 6,050,260 A | 4/2000 | Daniell et al. | |
| 6,055,984 A | 5/2000 | Brain | |
| 6,102,041 A | 8/2000 | Boussignac et al. | |
| 6,279,574 B1 | 8/2001 | Richardson et al. | |
| 6,305,374 B1 | 10/2001 | Zdrojkowski et al. | |
| 6,315,739 B1 | 11/2001 | Merilainen et al. | |
| 6,374,827 B1 | 4/2002 | Bowden et al. | |
| 6,394,093 B1 | 5/2002 | Lethi | |
| 6,457,472 B1 | 10/2002 | Schwartz et al. | |
| 6,539,940 B2 | 4/2003 | Zdrojkowski et al. | |
| 6,581,599 B1 * | 6/2003 | Stenzler | 128/204.23 |
| 6,655,382 B1 * | 12/2003 | Kolobow | 128/204.25 |
| 6,758,217 B1 | 7/2004 | Younes | |
| 6,948,497 B2 | 9/2005 | Zdrojkowski et al. | |
| 7,267,121 B2 * | 9/2007 | Ivri | 128/203.17 |
| 7,487,778 B2 * | 2/2009 | Freitag | 128/207.14 |
| 7,533,670 B1 * | 5/2009 | Freitag et al. | 128/204.23 |
| 7,562,657 B2 * | 7/2009 | Blanch et al. | 128/204.23 |
| 7,861,717 B1 * | 1/2011 | Krebs | 128/204.23 |
| 2001/0035185 A1 | 11/2001 | Christopher | |
| 2002/0020414 A1 | 2/2002 | Fukunaga | |
| 2002/0023645 A1 | 2/2002 | Zdrojkowski et al. | |
| 2003/0010339 A1 | 1/2003 | Banner et al. | |
| 2003/0145856 A1 | 8/2003 | Zdrojkowski et al. | |
| 2005/0034721 A1 | 2/2005 | Freitag | |
| 2005/0121038 A1 | 6/2005 | Christopher | |
| 2005/0224078 A1 | 10/2005 | Zdrojkowski et al. | |
| 2006/0060199 A1 | 3/2006 | Lampotang et al. | |
| 2007/0017518 A1 | 1/2007 | Farrugia et al. | |

FOREIGN PATENT DOCUMENTS

| | | |
|---|---|---|
| WO | 2007035804 A2 | 3/2007 |

\* cited by examiner

SYSTEM FOR PROVIDING FLOW-TARGETED VENTILATION SYNCHRONIZED TO A PATIENT'S BREATHING CYCLE

RELATED APPLICATION

The present application is a continuation of the Applicants' U.S. patent application Ser. No. 11/627,512, entitled "System For Providing Flow-Targeted Ventilation Synchronized To A Patient's Breathing Cycle," filed on Jan. 26, 2007.

BACKGROUND OF THE INVENTION

1. Field of the Invention

The present invention relates generally to the field of mechanical ventilation of patients. More specifically, the present invention discloses an open system for providing ventilation in a predetermined flow waveform synchronized to a patient's breathing cycle to augment respiration by a self-breathing patient.

2. Statement of the Problem

Standard mechanical ventilators deliver pressure. There are three classifications of mechanical ventilators that are based upon how they administer pressure ventilation. Negative pressure ventilation requires an apparatus that expands the chest wall, creating levels of sub-atmospheric pressure that draw air or oxygen-enriched ambient gas through the upper airway and into the lungs. Positive pressure ventilation requires that supra-atmospheric pressure is generated and controlled by the device so that air or oxygen-enriched air is pressurized to the degree that it can be forcibly driven through the upper airway and into the lungs. The third method is a combination of positive/negative pressure. The prime example is a high frequency oscillator, where oscillations of negative and positive pressure are produced in the airway in a sinusoidal pattern that is independent of self-breathing efforts and at a rate that exceeds the maximum human respiratory rate by many fold.

Positive pressure ventilators are by far the most frequently used mechanical breathing device. They can be further divided into invasive or noninvasive systems. Invasive systems utilize an endotracheal or tracheostomy tube, with an inflated tracheal cuff that creates an obstruction closing off the upper airway from atmospheric or ambient gas and thus creates a closed system between the positive pressure ventilator and the lungs. This is Closed System Positive Pressure Ventilation (CSPPV). Breath delivery with positive pressure ventilators can be categorized as either pressure-targeted or volume-targeted ventilation. Generation of a specific airway pressure on inspiration and often a different pressure on expiration are pressure-targeted outcomes, or alternatively, a level of pressure is generated to achieve the primary goal of a targeted tidal volume delivered to the lungs (volume-targeted ventilation). The closed system allows a positive pressure breath to be delivered through the inspiratory valve of the device, through the inspiratory limb of the breathing circuit and directly to the lungs without loss of pressure by dissipation of gas into the atmosphere. The delivery of the breath can be forced into the patient independent of the patient's breathing pattern (time triggering) or synchronized with the patient's effort to inhale (pressure or flow triggering), but the patient's normal negative pressure inspiration during self-breathing is lost as it is converted to a positive pressure breath. Peak inspiratory airway pressures of 20 to 30 cm $H_2O$ or greater are commonly achieved. The inspiratory valve is open during the patient's entire inspiratory phase. During inspiration the expiratory valve on the expiratory limb of the breathing circuit must remain closed to maintain the pressurized breath. The transition from inspiration to expiration is ultimately governed by the ventilator (breath cycling) and not the patient, because in a closed system, the expiratory valve must open to allow exhalation. During exhalation, the inspiratory valve is closed to prevent retrograde flow of gas back into the machine, which could result in the physiologic terms of rebreathing carbon dioxide or dead space gas, which is dangerous and potentially life-threatening. The expiratory valve is at least partially open to allow the breath to adequately vent into the atmosphere. The pressure at the onset of exhalation with CSPPV approximates the peak inspiratory pressure (e.g., 20 to 30 cm $H_2O$ or greater) and dissipates over the expiratory phase as a function of the patient's exhaled gas being allowed to exit through the exhalation valve. Though the expiratory valve or mechanism is often completely open during exhalation, partial closure of the expiratory valve or mechanisms during one or more components of the expiratory phase may achieve a targeted level of expiratory pressure within the lungs while still maintaining adequate exhalation through the valve and acceptable gas exchange Examples of methods to achieve pressure in the lungs during exhalation due to partial exhalation valve closure during one or more points in exhalation include expiratory retard and positive end expiratory pressure (PEEP). During CSPPV, the expiratory valve is not completely closed during exhalation as life-threatening excessive pressure and suffocation could result. Partial closure of the expiratory valve during end exhalation (PEEP) prevents the decline in airway pressure from ever returning to the 0 cm $H_2O$ baseline between exhalation and inhalation. Prescribed PEEP may be 5 to 15 cm $H_2O$ or more. On expiration, with CSPPV all the exhaled gas is routed through the expiratory limb of the circuit and is available to the ventilator for analysis. This analysis is required for proper ventilator function and monitoring. More than one CSPPV mode can be administered simultaneously (e.g., intermittent mandatory ventilation with pressure support and positive-end expiratory pressure).

Though CSPPV can be life-saving for patients who are unable to do any negative pressure self-breathing, there are a number of problems with the CSPPV technology. It has been scientifically demonstrated that the pressure generated by positive pressure ventilation can injure the delicate structures of the lungs. This injury can cause significant morbidity and mortality, particularly when CSPPV is superimposed upon acute lung injury from pneumonia or adult respiratory distress syndrome (ARDS). Over time, positive pressures that were once thought to be safe have been determined to cause lung injury. The safe positive pressure threshold that does not cause (or worsen) acute lung injury on some level is presently unknown. There is a scientific trend for documentation of acute lung injury with lower and lower positive pressures as more is learned about the pathophysiology of acute lung injury on organ, tissue, cellular, biochemical and genetic levels. In certain clinical settings positive inspiratory and/or expiratory pressures may impair gas exchange in the lungs. Positive pressure ventilation can cause life-threatening impairment of cardiac output and can cause lung collapse (tension pneumothorax) resulting from barotrauma.

Other issues associated with the endotracheal tube with inflated cuff that is required to maintain pressure with CSPPV can also cause serious injury such as tracheomalasia, tracheo-oesophageal fistula, tracheal granulation tissue and tracheal stenosis and necrosis. Along with serious injury, the inflated tracheal tube cuff has other consequences. Its use does not allow for communication between the larynx and the upper airway and causes gas to be channeled away from a patient's natural humidification system. This is detrimental to the patient. The inflated cuff prohibits utilization of the vocal cords. Patients are unable to speak causing poor communication between the patient and healthcare providers and family thus impeding proper informed consent and establishment of advanced directives. This absence of speech can cause frustration, anxiety and depression. Bypassing the larynx also impairs cough. Normal closure of the vocal cords allows generation of the glottic blast that facilitates effective cough and clearance of respiratory secretions. Finally, the vocal cords serve as a variable regulator of respiratory flow that fine tunes passage of gas in and out of the lungs to optimize gas exchange.

Use of an inflated cuff also pools upper respiratory secretions above the cuff and, over time, these secretions become contaminated with bacteria. These pooled secretions can leak into the lungs and increase the risk of ventilator-associated pneumonia (VAP). Additionally, inflated tracheal tube cuffs can impair swallow. Though tracheostomy tubes may be more comfortable, endotracheal tubes that pass through the nose or mouth and into the trachea are typically used initially and are very uncomfortable. Tracheostomy tubes require a surgical procedure that can result in a number of complications, including bleeding, infection, barotrauma and airway obstruction.

Liberating patients from CSPPV requires a successful return of the patient to normal negative pressure self-breathing. This has proven to be difficult, particularly when patients have had their breathing controlled and altered by CSPPV for greater than 21 days (prolonged mechanical ventilation, or PMV). In fact, once patients have required CSPPV for greater than 21 days, the wean success rate is only about 50% overall, with a range of 35% to about 60%.

In the past, efforts have been made to allow patients to speak through the upper airway during CSPPV. One method utilizes deflation of the tracheal tube cuff. This open system was not intended for use with standard CSPPV as inadequate ventilation can result. Use of this method may allow a significant portion of the ventilator breath intended for delivery entirely to the patient's lungs to escape through the upper airway. Modes that function based upon targeting a specific inspired tidal volume or pressure and expired pressure can be significantly compromised by the absence of connectivity of the ventilator to closed passages in and out of the lungs and inability of pressures measured in those passages to accurately reflect lung pressure, since pressure can freely dissipate via the upper airway. The volume and characteristics of the exhaled breath passing back to the ventilator in this type of open system will be inaccurate and could compromise the ventilator's ability to use properties such as exhaled tidal volume or airway pressure to evaluate proper ventilator delivery. Unnecessary triggering of alarms such as low pressure or inadequate expired breath volume may occur. Absence of a closed system may result in dys-synchrony between the ventilator and the patient if adequate feedback is not received by the ventilator regarding the patient's breathing efforts thus the ventilator is unable to adequately assess when to deliver the breath or when to terminate the breath. Such ventilator-patient dys-synchrony is known to have deleterious physiologic effects. Some modes such as pressure support ventilation may partially or completely compensate for the leak with the deflated cuff by increasing device driving pressure to maintain the desired pressure delivered to the lungs. However, use of the positive pressure ventilator by this method is still positive pressure ventilation and still pressure-targeted and not flow-targeted. The patient's negative pressure self-breathing is still converted to positive pressure breaths.

When the cuff is deflated, one-way inspiratory valves may be placed in the external CSPPV circuit to prevent gas from flowing back through the machine on exhalation. This is intended to direct expired gas up through the vocal cords to facilitate speech. However, many of the problems noted above that are encountered with using standard closed system CSPPV with an open system still remain. Use of the positive pressure ventilator by this method is still positive pressure ventilation and still pressure-targeted or volume-targeted and not flow-targeted. The patient's negative pressure self-breathing is still converted to positive pressure breaths.

Noninvasive ventilation does not require a tracheal tube with inflated cuff. Bi-level positive pressure ventilation generates a set positive pressure on both inspiration and expiration as the targeted outcomes (pressure-targeted ventilation). An interface such as nasal or nasal/oral mask, full face mask or nasal pillows or similar devices are required to create a barrier between the upper airway and the atmosphere. As with CSPPV, the patient's negative pressure self-breathing is converted to positive pressure breaths. The obstruction created by the interface is great enough that it allows generation of adequate positive pressure to provide all or nearly all of the patient's required breath. The obstruction created by the interface allows lung-distending pressure to be maintained on exhalation which is always less than the pressure on inhalation. The patient both inhales and exhales through the single-limb breathing circuit. As with CSPPV, exhalation of gas back into a circuit maintains proper ventilator function and monitoring. The gas delivery valve connected to the single limb breathing circuit is continuously open during inspiration and expiration to maintain desired inspiratory and expiratory positive pressures. The pressurized breath is triggered either when the patient makes an effort to breathe or time-triggered when a breath is not sensed and a specified time has passed. This prior art is referred to as Substantially Closed System Positive Pressure Ventilation (SCSPPV). Since the interface is usually not completely sealed, there is a leak of pressure and loss of a portion of the gas into the atmosphere. In addition to gas leak through the upper airway, the single limb circuit has an exhalation valve at the distal end that is constantly open during both inhalation and exhalation. The valve remains completely open during inspiration to flush $CO_2$ from the circuit and completely open on expiration to allow the exhaled breath to escape into the atmosphere. Rebreathed $CO_2$ can cause significant morbidity and mortality. Common exhalation valves or mechanisms include Whisper Swivel, Castle Port or NRV devices. Under no circumstances should the valve be occluded. The microprocessor constantly evaluates leaks by comparing pressure in the lumen of the proximal inspiratory circuit to pressure as measured through monitoring tubing in communication with the lumen of the distal end of the circuit. The microprocessor can also compensate by changing the driving pressure to maintain the primary target of delivered pressure (pressure-targeted ventilation) during inspiration and expiration.

With SCSPPV, the absence of a tracheal tube with an inflated cuff avoids a number of the previously described complications of CSPPV. However, the nasal or nasal/oral mask, full face mask or nasal pillows or other devices used with SCSPPV to serve as an interface between the upper airway and atmosphere can be uncomfortable. Skin ulcerations and abrasions can result from tight-fitting masks. Patients in respiratory distress may feel claustrophobic with these devices covering their nose, mouth or entire face. The devices can make speech difficult and eating and swallowing difficult as well. Devices covering the mouth or face can impair the patient's ability to expectorate sputum. Similar to CSPPV, a disadvantage of SCSPPV technology is the requirement for generation of pressure. Depending on the device, peak inspiratory pressures of up to 20 to 40 cm H$_2$O can be generated. The pressurized breath delivery can be uncomfortable. Current medical literature shows that SCSPPV may be neither effective nor tolerated in the extremes of mild and severe respiratory failure. In certain clinical settings positive inspiratory and/or expiratory pressures may impair cardiac output and gas exchange in the lungs. Though not as likely to occur as with CSPPV, acute lung injury and barotrauma may potentially occur when pressures in the high range are delivered. Similar to CSPPV, the use of SCSPPV eliminates normal negative pressure self-breathing. As with CSPPV, successful return to normal negative pressure self-breathing is required for successful discontinuation of SCSPPV.

Transtracheal augmented ventilation (TTAV) is a prior art that is an alternative to positive pressure ventilation. TTAV is not intended to give full ventilatory support like a CSPPV device, but augments the patient's self-breathing by utilizing an open system and delivering a constant and continuous flow of about 8 to 20 L/min of a heated and humidified air and oxygen blend to the lungs during both inspiration and expiration. It is an open system because there is no inflated tracheal cuff and no mask, nasal pillows or other device to create a complete or near complete barrier between the mouth and/or nose and the atmosphere. Because of the nature of the open system, delivered gas can easily escape into the atmosphere and positive pressure is not a targeted outcome. Tidal volume that the patient inspires through the device is not an outcome that can be reliably targeted because of volume loss through the upper airway and variability of volume that the patient inspires through the upper airway during negative pressure self-breathing. In fact, TTAV is only intended for use on patients who are able to do some degree of negative pressure self-breathing. Benefits from augmented ventilation are derived from a defined constant and continuous flow that is superimposed upon the patient's own breathing cycle. Patients can freely inhale room air through the mouth and nose in addition to the gas delivered by the TTAV device. With prior art, air or oxygen enriched air can be delivered directly into the trachea via a transtracheal catheter. The delivery device heats and humidifies the gas to eliminate complications and sequellae from the humidity deficit that would otherwise occur from delivering constant and continuous flows of 8 to 20 L/min of dry cool gas directly into the trachea. There is a single inspiratory circuit with no expiratory circuit or expiratory valve because the patient is free to exhale normally through the nose and mouth. No inspiratory valve is used as a constant and continuous flow is delivered to the patient rather than distinct breaths. Since the constant and continuous flow is superimposed upon the patient's inherent negative pressure self-breathing cycle, synchronization with the patient's breathing is not required. A pressure relief valve prevents over-pressurization within the device in the event of a malfunction or obstruction and an alarm signals the event. Exhalation of gas back into the breathing circuit or into the device is not required to monitor or manage gas delivery during routine operation.

Compared to either low flows used with prior art transtracheal oxygen therapy or mouth breathing without transtracheal flows, potential physiologic benefits of TTAV at a constant continuous flow of 10 L/min include correction of hypoxemia, reduced inspiratory work of breathing, decreased volume of gas the patient must inspire through the upper airway, and improved exercise capacity. The effect of constant continuous TTAV flow above 10 L/min corrects hypoxemia. Since prior studies show that the relationship between flow and response is directly related, one would predict improved response in terms of reduced inspiratory work of breathing, decreased volume of gas the patient must inspire through the upper airway, and improved exercise capacity with flows above 10 L/min. However, the effect on these specific physiologic parameters has not been specifically evaluated. Compared to low flow transtracheal oxygen therapy at 1.5 L/min, potential physiologic benefits of TTAV at a constant and continuous flow of 15 L/min additionally include increased efficiency of breathing, reduced total minute ventilation and reduced end-expiratory lung volume. The effect of constant and continuous TTAV flow above 15 L/min on these physiologic parameters has not been evaluated. Reduced physiologic dead space is seen with low flow transtracheal oxygen (up to 6-8 L/min) as compared to mouth breathing. However, it is not known if constant and continuous flow above 8 L/min with TTAV results in any further reduction in physiologic dead space. TTAV at 10 L/min as a means of augmenting ventilation of patients with chronic respiratory failure during nocturnal home use has been shown to be safe and effective. Furthermore, removal of prolonged mechanical ventilation patients from CSPPV and placement on a constant and continuous TTAV flow from 10 to 15 L/min through a catheter placed within the lumen of a deflated cuff tracheostomy tube has been shown to improve wean success from CSPPV. In this setting, use of the TTAV device and CSPPV device are alternated in an iterative fashion, with a progressive increase of time on TTAV. With the cuff deflated while the patient is on the TTAV device with a constant and continuous flow of 10 L/min, all gas is expired through the glottis and upper airway resulting in the previously described benefits associated with restored speech, more effective cough and return of glottic function as a physiologic variable regulator of respiratory flow. As noted previously, the inflated tracheal cuff prevents these benefits from occurring with CSPPV. It is unknown if constant and continuous TTAV flow above 15 L/min improves effectiveness or wean outcome.

A less than optimal condition associated with TTAV is that a constant and continuous flow is administered throughout the inspiratory and expiratory phases of the respiratory cycle. Each of the potential benefits as described above will likely have different respiratory cycle targeted flow rates and waveforms to achieve maximal beneficial effect in a given patient, and requirements may change with alterations in the clinical status of that individual over time. Additionally, patients with different diseases or disorders may benefit more from certain physiologic effects than from others, and those effects can be influenced by different flows and flow waveforms administered in specific phases (or phase components) of the respiratory cycle. Synchronizing the amount and pattern of flow with specific phases of the breathing cycle or even components of phases of the breathing cycle may markedly influence clinical efficacy. In contrast, constant continuous flows delivered throughout the inspiratory and expiratory phases as seen in the prior art may not be efficacious. For example, a constant and continuous flow of 40 L/min delivered throughout the inspiratory phase of breathing may significantly increase total inspiratory work of breathing rather than reduce it if the specific physiologic effect on the respiratory inspiratory phase and phase transitions as well as the phase components are not considered. With prior TTAV art, that constant and continuous flow of 40 L/min would also be delivered during exhalation. That amount of flow throughout expiration would likely impose a significant expiratory workload causing the patient to forcibly exhale against the constant incoming stream of tracheal gas. This could result in respiratory muscle fatigue and impaired gas exchange. There may be benefit to transiently interrupting flow during certain components of the breathing cycle which could influence clinical efficacy. TTAV with a constant and continuous flow eliminates the potential for improving safety, efficacy and tolerance by the inability of the prior art to target non-constant, potentially non continuous flows with different peak flows and flow patterns that are strategically synchronized with the various phases or components of the phases of a patient's breathing cycle.

Another weakness associated with conventional TTAV systems is that, other than an alarm and pressure relief valve for excessive pressures encountered within the channels of the delivery device and lumen of the circuit, there are no sensors or measurement devices that provide physiologic data that identify phases or components of phases of the patient's negative pressure self-breathing cycle that are designed to regulate breath synchronized, flow-targeted delivery. Conventional TTAV systems do not have microprocessors supporting breath-synchronized, flow-targeted delivery designed to manage patient physiologic data, display the data, trigger alarms for out of range results or incorporate that information into intelligent processing for a feedback loop or servo controlled device response to the physiologic data. Another problem with conventional TTAV systems is that the only clinical implementation to date has been limited to use with a transtracheal catheter.

The prior art also includes ventilation systems based on "flow triggering" a breath that is subsequently supported by CSPPV. As opposed to a drop in circuit/ventilator pressure indirectly indicating a breath effort by a patient, the CSPPV breath is triggered by a presumed effort by the patient to generate inspiratory flow. Though patient inspiratory flow is not directly measured, the breathing effort is presumed because flow inside the expiratory limb is measured to drop to less than the known pass through, or bias flow through the circuit. Flow triggering requires a dual inspiratory/expiratory limb circuit. At some point in the mid to late expiratory phase, the ventilator delivers a predetermined constant flow that circulates through the inspiratory and expiratory limb of the circuit and out through the open expiratory valve. With flow triggering the inspiratory valve or mechanism is partially open in the transition phase between exhalation and inhalation, allowing low flows concurrent with the patients inspiratory effort to enhance triggering sensitivity of the machine. Flow is measured at both the proximal connection of the inspiratory limb and near the expiratory valve. Any drop in flow is assumed to represent the patient's effort to breathe in gas, and the inspiratory breath is triggered. Though flow through the ventilator circuit may reduce the work the patient has to do to draw in an initial portion of the breath to trigger the ventilator, the delivered breath is still positive pressure generated and is either pressure or volume targeted.

One very different type of CSPPV mode is High Frequency Jet Ventilation (HFJV). A pulsating (non-continuous) jet is delivered via a catheter placed within a tracheal tube with inflated cuff. The pulsing volume is determined by setting a driving pressure in pounds per square inch (e.g., 30 psi) and the set rate is multiples of the patient's breathing rate (e.g. 150 breaths per minute) and not synchronized with the patient's efforts. A second source of gas flow is available from the ventilator circuit that can be drawn into the tracheal tube directly through the patient's breathing efforts or indirectly drawn in by a venturi effect from flow through the device. Gas that passes through the circuit and past the patient's airway must exit through, at minimum, a partially open exhalation valve. Gas exhaled by the patient must also exit via the exhalation valve.

HFJV is different than the present invention for a number of reasons. First, it is a form of Positive Pressure Ventilation (PPV) (i.e., pressure-targeted). Gas is delivered in discreet boluses in a rapid manner not synchronized with the patient respiratory cycle. It is a closed system with the exhalation valve partially or completely open during exhalation. Finally, a second lumen is required to deliver additional flow to the patient.

Another technology that utilizes a catheter placed within a cuff-inflated tracheal tube during concurrent CSPPV is called Tracheal Gas Inflation (TGI). TGI is different than the present invention because, in addition to a delivered CSPPV mode via the tracheal tube, an additional flow of gas is insufflated into the trachea via a catheter in a closed system with the cuff inflated. As with HFJV delivered with CSPPV, a second source of gas is supplied via a second lumen, and gas that exits the patient must exit the exhalation valve. The exhalation valve is partially or completely open during exhalation. With TGI, the second lumen delivers standard CSPPV breaths concurrent with flow through the tracheal catheter. Thus, TGI is a mode delivered in conjunction with one or more CSPPV modes.

3. Solution to the Problem

The present invention provides an open system for flow-targeted ventilation to augment the respiration of a self-breathing patient. A predetermined flow waveform is delivered to the patient's airway in synchronization with the patient's breathing cycle and at a sufficient flow rate to achieve a desired physiologic outcome, such as mitigating pressure in the patient's airway, reducing the patient's work of breathing, flushing carbon dioxide from the patient's airway, and increasing blood oxygenation. The present system can also be integrated into CSPPV and SCSPPV devices. For example, one goal of integrating or combining the present system with PPV in one device is to eliminate the iterative steps of switching the patient back and forth between two separate devices to achieve a needed clinical outcome. Another goal is to improve access of certain patient populations to the medical benefits of the present invention while eliminating the need for capitalization of a separate device. This controls cost, reduces redundancy of delivery devices, increases efficiency, saves space at the patient bedside and improves resource allocation.

The present system is intended to augment ventilation by superimposing continuous, non-constant and, under some conditions, non-continuous flows upon the spontaneous negative-pressure self-breathing of patients. Unlike prior art pressure-targeted or volume-targeted positive pressure ventilation, this invention is flow-targeted because achievement of specific flows and flow waveforms are the targeted outcome. Clinician-defined flows are targeted for specific phases or components of phases of the patient's breathing cycle in order to achieve one or more physiologic improvements. Unlike CSPPV or SCSPPV where positive pressure is either the targeted endpoint or an expected consequence of volume-targeted ventilation, the present invention uses an open system and avoids generation of positive pressures that can cause patient discomfort and injury. Specially designed tubing airway devices maintain an unobstructed interface between the airway and atmosphere. A variety of sensors can be used to detect properties associated with phases of the patient's breathing cycle. A microprocessor receives and processes the data generated by the sensors for intelligent monitoring and regulation of the present system.

In the presence of respiratory distress, the invention mitigates the negative-pressure swings that the patient with respiratory compromise must generate during inspiration and the positive-pressure swings that must be generated during expiration with certain diseases and disorders. These pressure swings result from increased work of breathing (WOB). The present system can mitigate the patient requirement for generating pressure, and can thus mitigate excessive WOB, while still allowing the patient to self-breathe in an open system without the need for CSPPV or SCSPPV. With certain diseases or disorders the patient may benefit by not attempting to inspire through the upper airway at all, but compensate by closing the vocal cords (glottis) and mouth and passively letting the device inflate the lungs at the prescribed flow and flow pattern. Though some pressure is generally encountered, it is not the primary target of the device output and muscular work by the diaphragm and thoraco-abdominal muscles is not required to generate pressure. Thus, the system mitigates a pressure that would be generated by the patient as a result of WOB. The free-breathing patient determines when the transitions between inspiration and expiration occur.

SUMMARY OF THE INVENTION

This invention provides an open system to deliver breath-synchronized, flow-targeted ventilation to augment respiration by a self-breathing patient. A sensor detects a physical property of a patient's respiratory cycle. A processor monitors the sensor and controls a gas source to deliver oxygen-containing gas through a tube extending into the patient's airway with the flow rate varying over each inspiratory and expiratory phase of the respiratory cycle in a predetermined non-constant waveform synchronized with the respiratory cycle to augment the patient's spontaneous respiration. Gas is delivered at a flow rate sufficient to significantly mitigate the airway pressure the patient must generate during spontaneous breathing and thereby reduce the patient's work of breathing.

These and other advantages, features, and objects of the present invention will be more readily understood in view of the following detailed description and the drawings.

BRIEF DESCRIPTION OF THE DRAWINGS

The present invention can be more readily understood in conjunction with the accompanying drawings, in which.

DETAILED DESCRIPTION OF THE INVENTION

Figure 1:
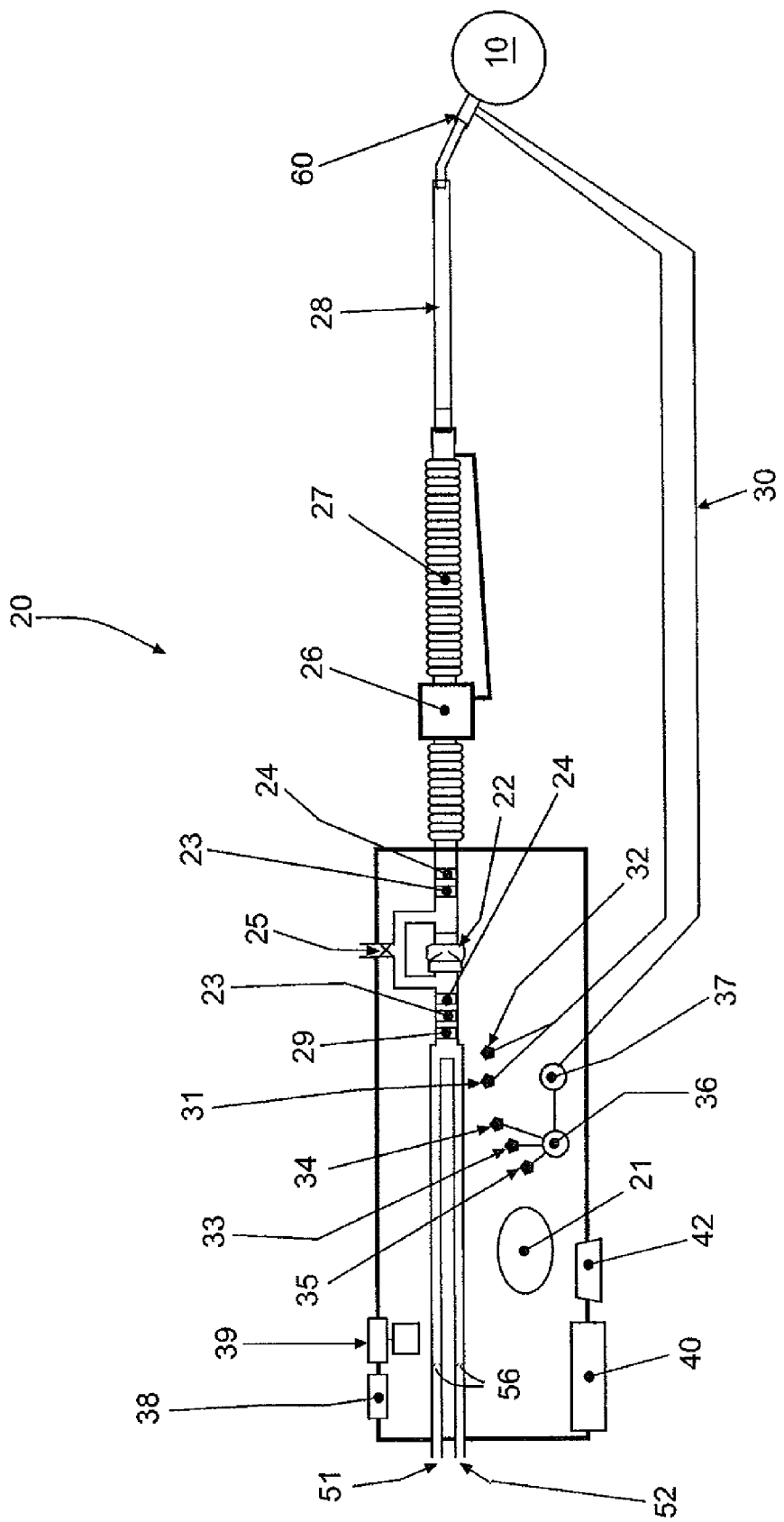
FIG. 1 is a simplified diagram of an embodiment of the present system using external air and oxygen supplies.

A basic configuration of the present system is shown in FIG. 1. In contrast to CSPPV devices, there is only one limb to the circuit. There is an inspiratory circuit, without the presence of a "Y" connector or an expiratory circuit, or expiratory valve. Unlike SCSPPV devices, there is not an expiratory valve located on the single limb circuit. Since the expiratory limb is not present, the flow, pressure or other sensing devices connected to the expiratory limb of the CSPPV device are not necessary.

In this embodiment, the single limb inspiratory delivery circuit passes through a system that heats and/or humidifies the gas delivered to the patient 10. In the preferred embodiment the gas is delivered through a servo temperature-controlled humidifier 26 with a heated breathing circuit 27 that delivers gas within an approximate predefined temperature range (approximately 34-38 degrees centigrade) and relative humidity (approximately 70 to 100%). The circuit 27 may be heated by a wire, circulating water, or similar means or the tubing may be insulated by a chamber of air or other means. Under each alternative configuration, the heated and/or humidified circuit 27 may either be connected to the patient airway interface 60 directly or through an interposed mid-section hose 28 as illustrated in FIGS. 1-5.

The patient airway interface 60 may include a variety of tubes placed within the airway, including, but not limited to a tracheostomy tube, tracheal catheter, tracheal catheter within a tracheostomy tube, endotracheal tube, nasopharyngeal catheter, endotracheal catheter, endotracheal catheter within an endotracheal tube, or nasal cannula or catheter. The patient airway interface 60 may have one or more sensors or sampling tubing/devices that can be attached or integrated into the outside wall of the tube. Since, unlike CSPPV where breathing only occurs through the inner lumen of the cuffed tracheal tube, the present device delivers flow through the lumen of the tube (e.g., a catheter), while allowing self-breathing with additional flow in and out through the upper airway and around the tube. Particularly during inhalation, the gas entering around the tube can be evaluated to measure or estimate the quantity and properties of the patient's self-generated portion of the breath. Similarly, the gas exiting around the tube can be used to measure or estimate the quantity and properties of the patient's exhaled breath, particularly with physiologic measurements such as $CO_2$ concentration. Devices such as an oximeter 31 or tissue $CO_2$ sensors can be attached to the airway interface 60, in particular where the device comes in contact with skin or airway mucosal surface or similar body surfaces (such as the tissue interface of a tracheal stoma). This is discussed in greater detail below with regard to FIGS. 6-18. As an alternative embodiment, one or more sensors or sampling tubing/devices can be attached or integrated into the inner wall of the tube or connection of either the mid-section hose 28 or heated circuit 27 to the tube.

Measurements could include internal pressure at the distal end of the device and the delivered temperature, humidity, flow or $F_1O_2$ or other gas properties (e.g., nitric oxide or helium concentration). One or more sensors or measuring devices can be located on, within or adjacent to the patient airway interface 60 as described above, and data can be electronically transferred back to the device (wired or wireless transmission of various forms). Examples include an ultrasonic probe, light emitting device, oximeter 31 or tissue $CO_2$ probe, thermistor 32 or other flow sensing device. Alternatively, a sampling tubing 30 can be used to transfer pressure back into the ventilator system 20 for measurement using a pressure transducer 33, as illustrated for example in FIGS. 1-5. When the purging pump 37 is disengaged by a valve or other mechanism, a valve assembly or similar device can additionally bypass the aspiration pump 36 and pressure within the gas sampling tube 30 can be in free communication with the pressure transducer 33. The pressure differential can be used to determine flow using an additional transducer 34. The sampling tubing 30 can be used to draw sampled gas back into the device for measurement through use of an aspiration pump 36 or some similar mechanism with optional periodic purging of the line with air or a liquid (e.g., saline or water) using a positive pressure pump 37 or similar purging device. The aspiration pump 36 would deliver the sample to sensor/measurement devices within the present device. Examples of sensor/measuring devices include a helium, nitric oxide, oxygen or $CO_2$ analyzer 35.

Data generated by sensors at or near the patient airway interface 60 and data generated by sensors within the ventilator system 20 from samples collected at or near the airway interface 60 and data generated from sensors, such as an oxygen analyzer 29, pressure transducer 24 and flow transducer 23 incorporated into the gas delivery mechanism of the system 20 are electronically transferred to the processor 21 through analog-to-digital conversion as needed, so digital information either reaches the processor or is converted from analog to digital at the processor 21. The processor 21 is typically in bidirectional or two-way communications with the entire sensing/measurement system (including sensors, aspiration and purging systems). The processor 21 also governs any necessary valve control, output regulation, calibration, quality control or operation status and self-test or auto-regulation information. In particular, at least one of the sensors measures a physical property (e.g., pressure, flow or carbon dioxide level) associated the patient's respiratory cycle. It should be understood that the processor 21 can be a microprocessor, controller or any other suitable type of hardware with sufficient intelligence to monitor the sensors, detect a desired phase (or phase component) of the patient's respiratory cycle, and control the ventilation system to deliver a predetermined flow profile of oxygen-containing gas varying over each inspiratory and expiratory phase of the respiratory cycle.

As another embodiment of the invention (not shown), one or more of the sensor/measurement devices, aspiration and purging systems and related hardware/software can be external and removably attached to the present device with appropriate ports 38 and 39 to connect the device or devices to communicate with the processor 21 and sensors measurement devices and sampling tubing located on or adjacent to the patient airway interface 60. Furthermore, devices in communication with the present device could include monitors such as pulse oximeters and tissue $CO_2$ monitors. In addition to sensor and measurement devices at or adjacent to the patient airway interface 60, other sensor and measurement devices can be integrated within the delivery system of the present device.

Oxygen-containing gas can be made available to the delivery system from a variety of gas sources, as shown in FIGS. 1-5. For example, FIG. 1 illustrates an external oxygen supply 51 from potentially a number of sources (including, but not limited to piped wall oxygen, direct liquid or compressed gas source, or concentrator). There is also an external source 52 of air (such as piped wall air, direct air compressor or blower source) or other medical gases including, but not limited to helium or nitric oxide by a variety of delivery means). Though not limited to this application, the system would likely be used in a hospital or similar institutional setting.

Figure 2:
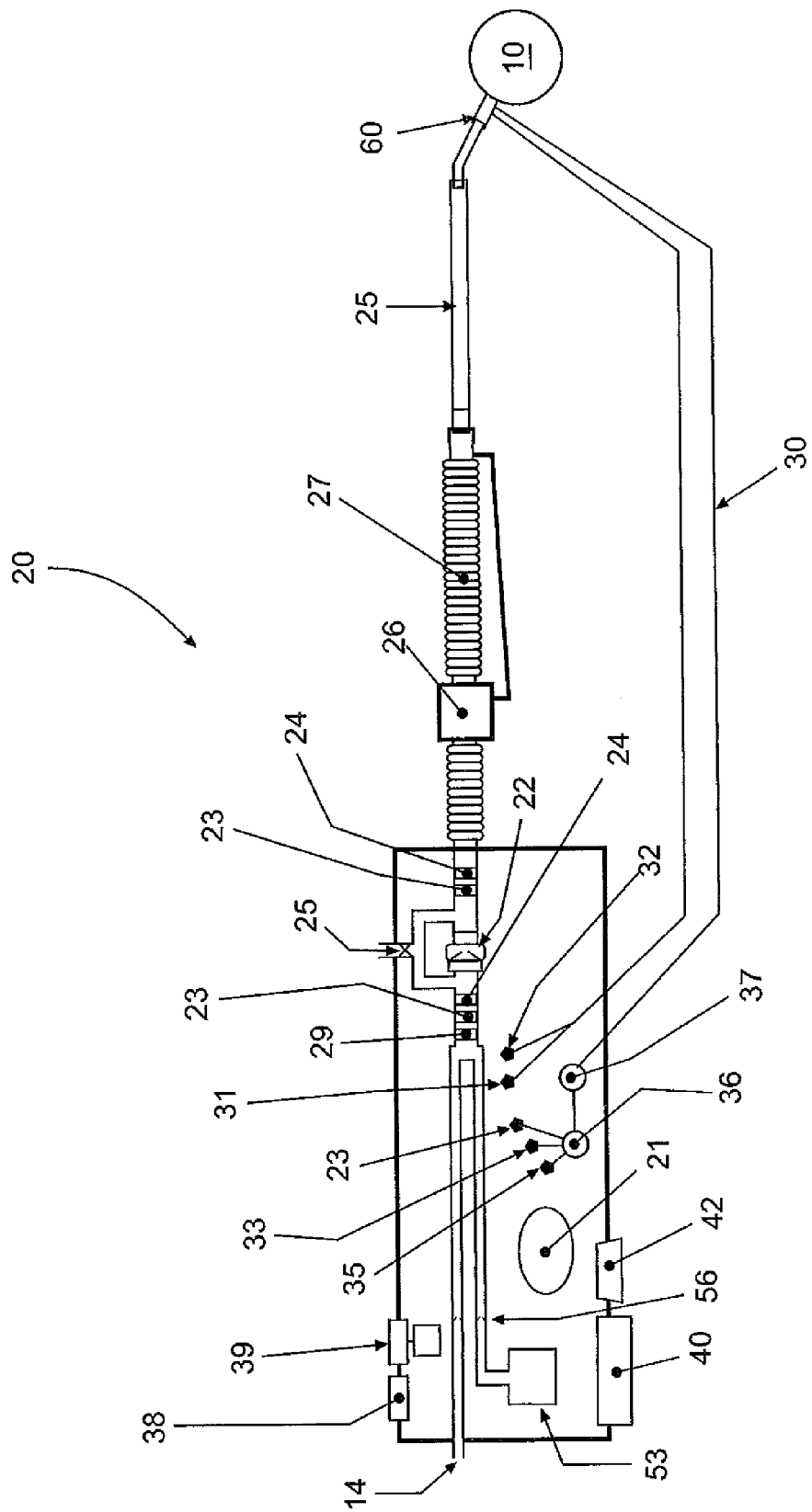
FIG. 2 is a simplified diagram of an embodiment of the present system that uses an external oxygen supply but has an internal blower/compressor to supply air.

FIG. 2 demonstrates an external oxygen source 51 similar to FIG. 1, In contrast, an air compressor, blower or similar air source 53 is housed within the present system. Though not limited to this application, the system would also likely be used in a hospital or similar institutional setting.

Figure 3:
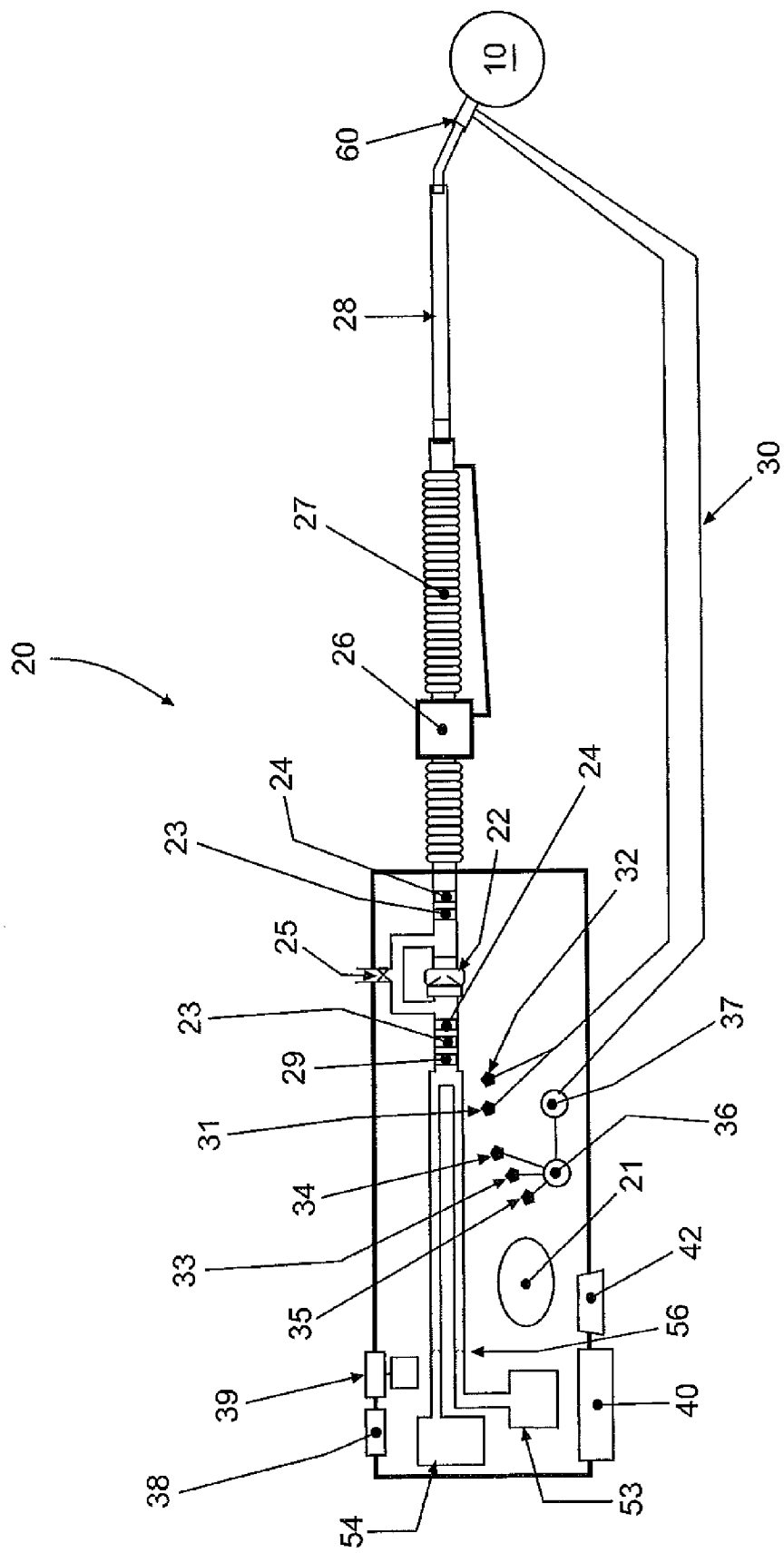
FIG. 3 is a simplified diagram of an embodiment of the present system having an internal blower/compressor and an internal oxygen concentrator.

FIG. 3 shows delivery of air by an internal air compressor or blower 53 or similar air generating device as noted in FIG. 2. However, oxygen is supplied by an internal oxygen concentrator 54 or comparable oxygen generating device that is housed within the present system. This embodiment could be use in either the home or a hospital or similar institutional setting.

Figure 4:
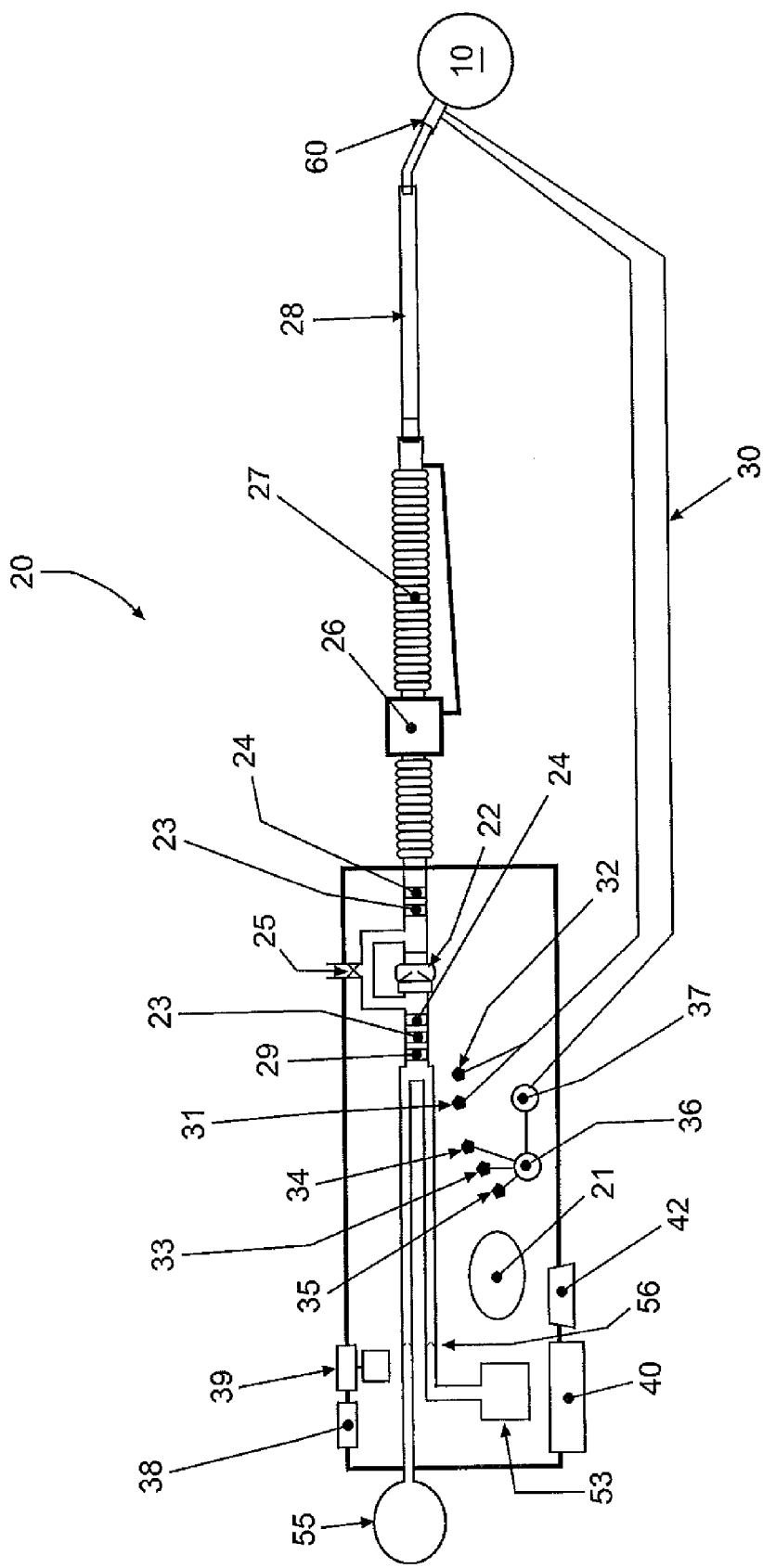
FIG. 4 is a simplified diagram of an embodiment of the present system having an internal blower/compressor and an external oxygen supply such as a compressed gas cylinder, liquid source or oxygen concentrator.

FIG. 4 illustrates the embodiment of an internal air compressor or blower 53 or similar air generating device and external delivery of oxygen into the proximal limb of the internal flow delivery system through use of an external compressed gas cylinder 55, liquid source, concentrator or comparable system. This embodiment may be most appropriate for a setting such as the home or nursing home setting.

Figure 5:
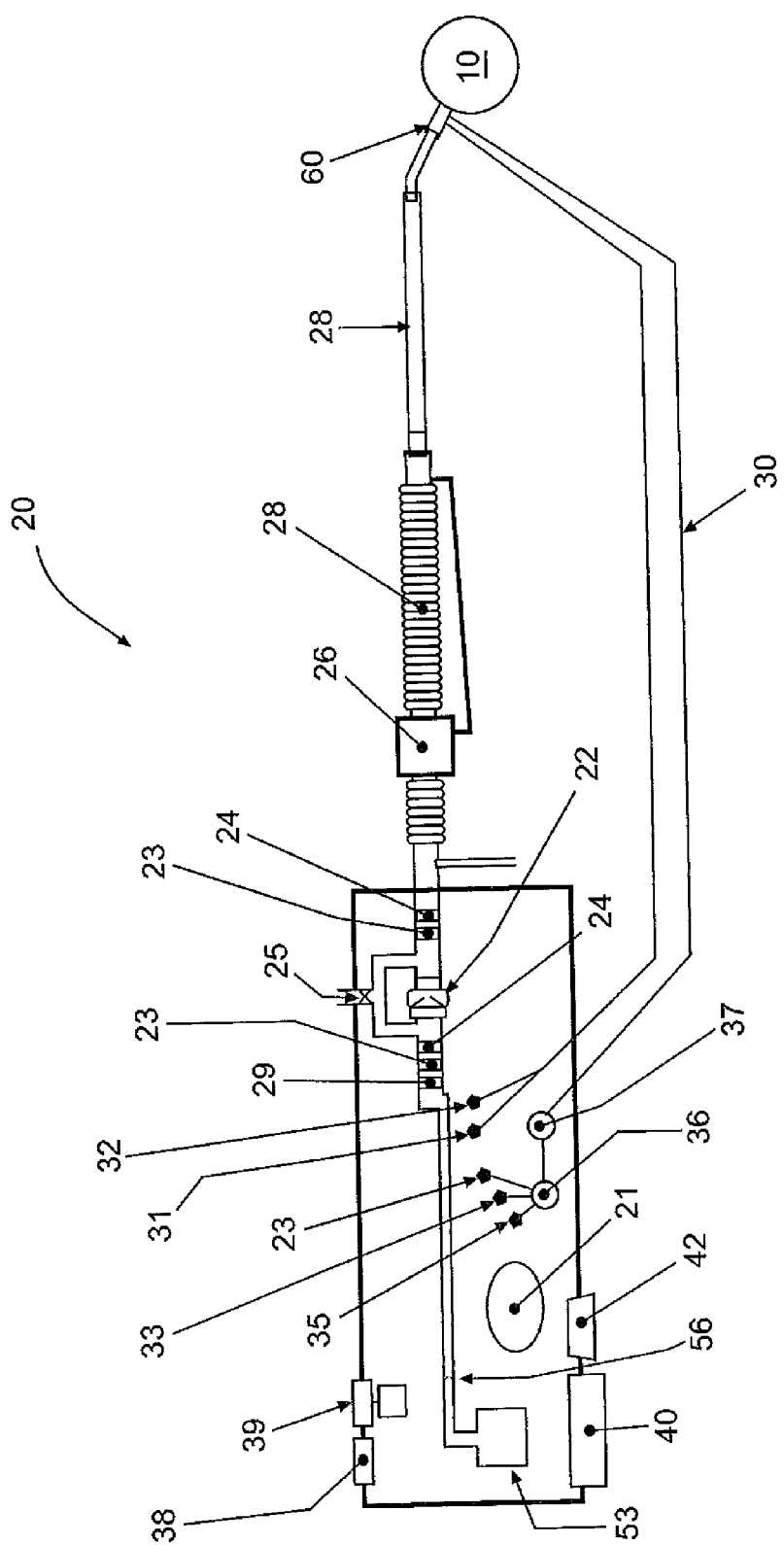
FIG. 5 is a simplified diagram of an embodiment of the present system having an internal blower/compressor and external delivery of oxygen through a connection into the delivery circuit leading to the patient.

FIG. 5 denotes an internal air compressor or blower 53 or similar air generating device and external delivery of oxygen with a T-connection or an equivalent connection into the delivery circuit distal to the present system. Sources could be (but not limited to) an external compressed oxygen gas cylinder or liquid oxygen source or oxygen concentrator. This embodiment may also be most appropriate for a setting such as the home or nursing home setting. Whether generated by examples illustrated in FIGS. 1-5 or variations thereof, the gas composition from those respective sources is regulated by one or more gas supply valves 56. Examples are shown in FIGS. 1-5 that regulate the mixing of concentrations and proportionate flow into the system. Concentrations of gas delivery can be confirmed by analyzers for the appropriate source such as oxygen, helium or nitric oxide.

The inspiratory valve 22 noted in FIGS. 1-5 regulates the maximum or peak flow and the associated flow waveform under the control of the processor 21. Flow transducers 23 can be placed proximal, distal or preferably both proximal and distal to the inspiratory valve 22. A pressure transducer 24 or other pressure sensing/measuring device is preferably located proximal to the inspiratory valve 22 to measure pressure and detect excessive machine pressure. Additionally, the preferred embodiment also incorporates a pressure transducer 24 or other pressure sensing/measuring device that is preferably located distal to the inspiratory valve 22 to measure pressure and detect excessive pressure within the flow delivery circuit. As shown in FIGS. 1-5, a conduit before and a conduit after the inspiratory valve merge into a conduit that has a pressure relief valve 25 that vents to the atmosphere, preventing excessive pressure build up within the present device or within the flow delivery circuit. Other configurations accomplishing the same outcome apply. Data from all of the sensors, valves, monitoring, measurement devices or other systems are passed on to the processor 21 and the processor 21 is preferably in bidirectional communication with those devices and multiple communications can occur simultaneously among the processor 21 and other systems.

The processor 21 is also in two-way or bidirectional communication with a local and optional remote graphic user interface 40 (GUI) or similar device with control panel, and with a local or optional remote audio alarm system 42. The GUI display 40 allows the user to set flow-targeted parameters, including peak flow, or any of the instantaneous flow waveform characteristics that can be targeted for a respiratory phase or component of a respiratory phase. Respiratory phases include an inspiratory phase, a transition phase from inspiratory to expiratory, an expiratory phase, and a transition phase from expiratory to inspiratory. Additionally, there are components to both the inspiratory and expiratory phases. In one embodiment, those flow-targeted peak flows (e.g., inspiratory and expiratory or optional peak transition flows) and relative flow waveform examples of described flows targeted to phases or components of the phases can be graphically presented to the user as options (among other flow pattern options) for selection. Selected "Help" screens could walk the user through various decision trees, such as selection of phase-related peak flows and flow patterns based upon specific management goals. The operator GUI 40 or other control interface allows the user to assess, measure, monitor, adjust or alter any parameter chosen by the user. The primary targeted parameter is peak flow and the associated flow pattern. However, the user can adjust for secondary parameters including, but not limited to delivered gas oxygen concentration, as well as the concentration of other medical gases such as air, helium, or nitric oxide, and the delivered temperature and humidity.

Though the system is flow targeted, every ventilation system must have secondary, or fail safe back-ups. As with other ventilation systems, excessive internal pressures within the present device or within the flow delivery circuit can be measured. Similarly, sensors, measuring devices and/or gas sampling tubing attached to, or associated with the airway interface device 60 can integrate with the present system to sense over-pressurization within the patient airway. The GUI interface 40 can allow the user to select default or custom pressure limits, and pressure exceeding that limit at any point will be dissipated (e.g., through the pressure relief valve noted in FIGS. 1-5) with the appropriate audible alarm 42 and visual alarm. The intelligent processor 21 can utilize data from all valves, sensors, measurement devices or other systems integrated within or in communication with the present device to perform calibration, quality assurance checks, other automatic tests or evaluations and to make automatic adjustments and compile reports.

The processor 21 can use data from the sensors, measurement devices or sampling tubing on, within or adjacent to the patient airway interface devices 60 to determine the phases and components of phases of the respiratory cycle of the self-breathing patient 10. Examples include, but are not limited to, flow (e.g., thermistor or differential pressure assessment), airway pressure and airway $CO_2$ waveform analysis. Airway $CO_2$ waveform analysis is a preferred embodiment, especially for tracheal tubes and tracheal catheters, as sampling of gas near the carina can eliminate a substantial portion of physiologic or "wasted" dead space, a known confounding factor in end-tidal capnography accuracy. The waveform will not only identify phases and components of phases of the respiratory cycle, but can serve as real time breath-by-breath analysis and/or trending of the adequacy of ventilation in the self-breathing patient 10 supported by the present invention.

Assessment of flow (and related volume) during inspiration that is contributed by the present invention and also self-breathed by the patient 10 would be clinically useful. The flow delivered by the present system during the time of inspiratory phase ($T_I$) and related volume can be calculated by the processor 21. Qualitative flow drawn in through the upper airway can be assessed by a thermistor attached to the outside of the airway tube. Alternatively, two pressure-sensing tubes of different lengths along the outside of the tube allow the system to measure differential pressure. This can be used by the processor 21 to present a qualitative assessment of flow drawn in through the upper airway. Given the patient characteristics (e.g. sex, height, race, age or other parameters), the processor 21 can calculate the area of the trachea based on known anatomical relationships. With additional input of the tracheal tube external diameter, the processor 21 can calculate the area between the outside of the tube and the tracheal wall through which the patient 10 is breathing between the two pressure measurements. The processor 21 can model and calculate the flow (and related volume) during inspiration that is contributed by the self-breathing patient 10. As an alternative, one or more ultrasonic probes can be placed on the outside of the tube to measure and calculate the area between the tracheal mucosa and tube. In summary, these measurements, along with the known properties of the tube (such as the surface area of any fenestrations) could be used with the pressure differential to calculate flow, and integrate flow into volume. As needed, corrections can be made for temperature, humidity, gas concentration and other factors. Using the same principle, flow and volume of the exhaled gas can be assessed. Various processor calculations of physiologic parameters can be presented to the user through the GUI 40 to present the respiratory-cardio physiologic status of the patient 10, including such assessments as volumetric carbon dioxide. Acceptable ranges can be set by the user, with GUI 40 and audio alarms 42 set to alert exceptions. With the intelligent processor 21, device monitoring information and physiologic data can input into a feedback loop that allows the invention to make specific adjustments based upon monitoring and physiologic data criteria determined by the user. The user can set appropriate limits with an appropriate local or remote GUI 40, and audible alerts and alarms 42.

Figure 6:
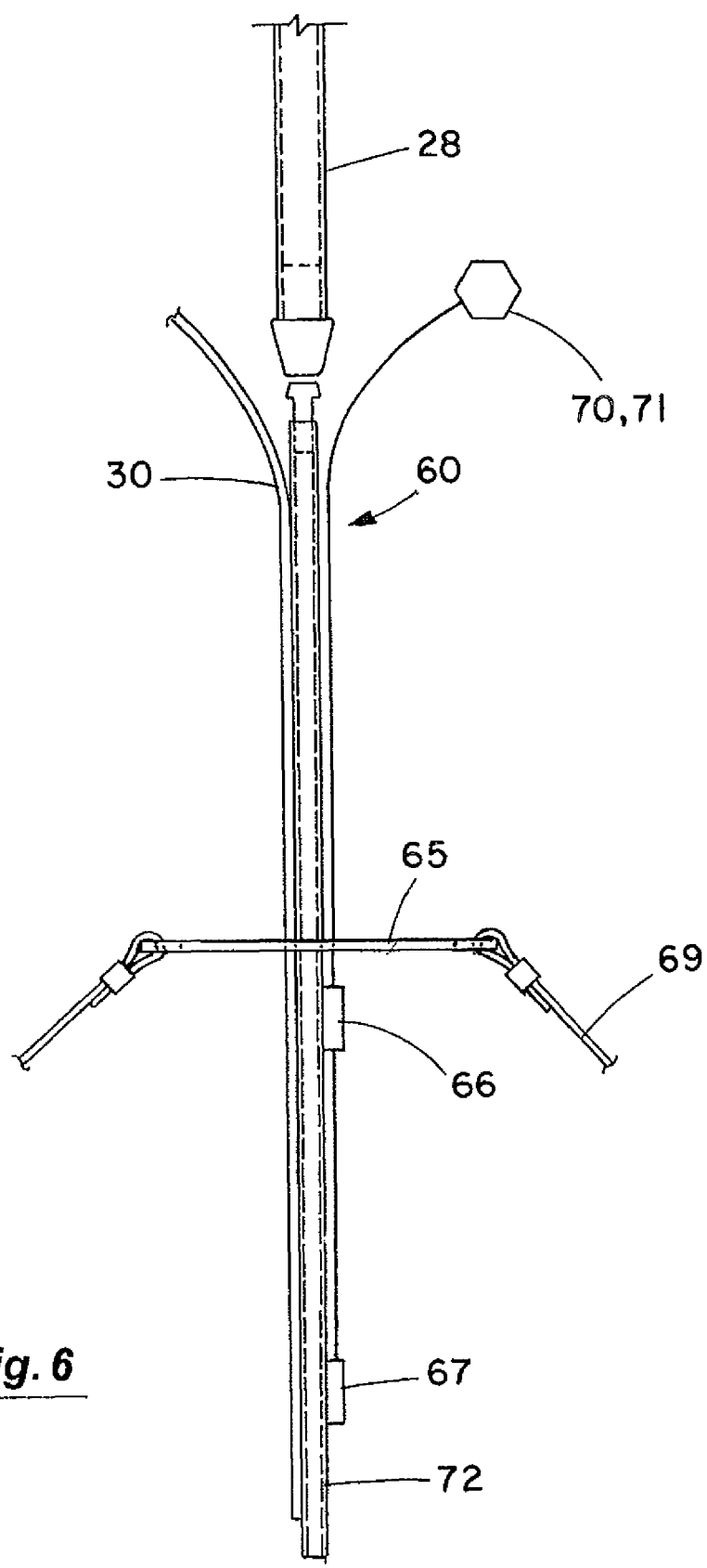
FIG. 6 is a cross-sectional view of an embodiment of an airway interface 60 intended for use as a tracheal catheter assembly.
Figure 7:
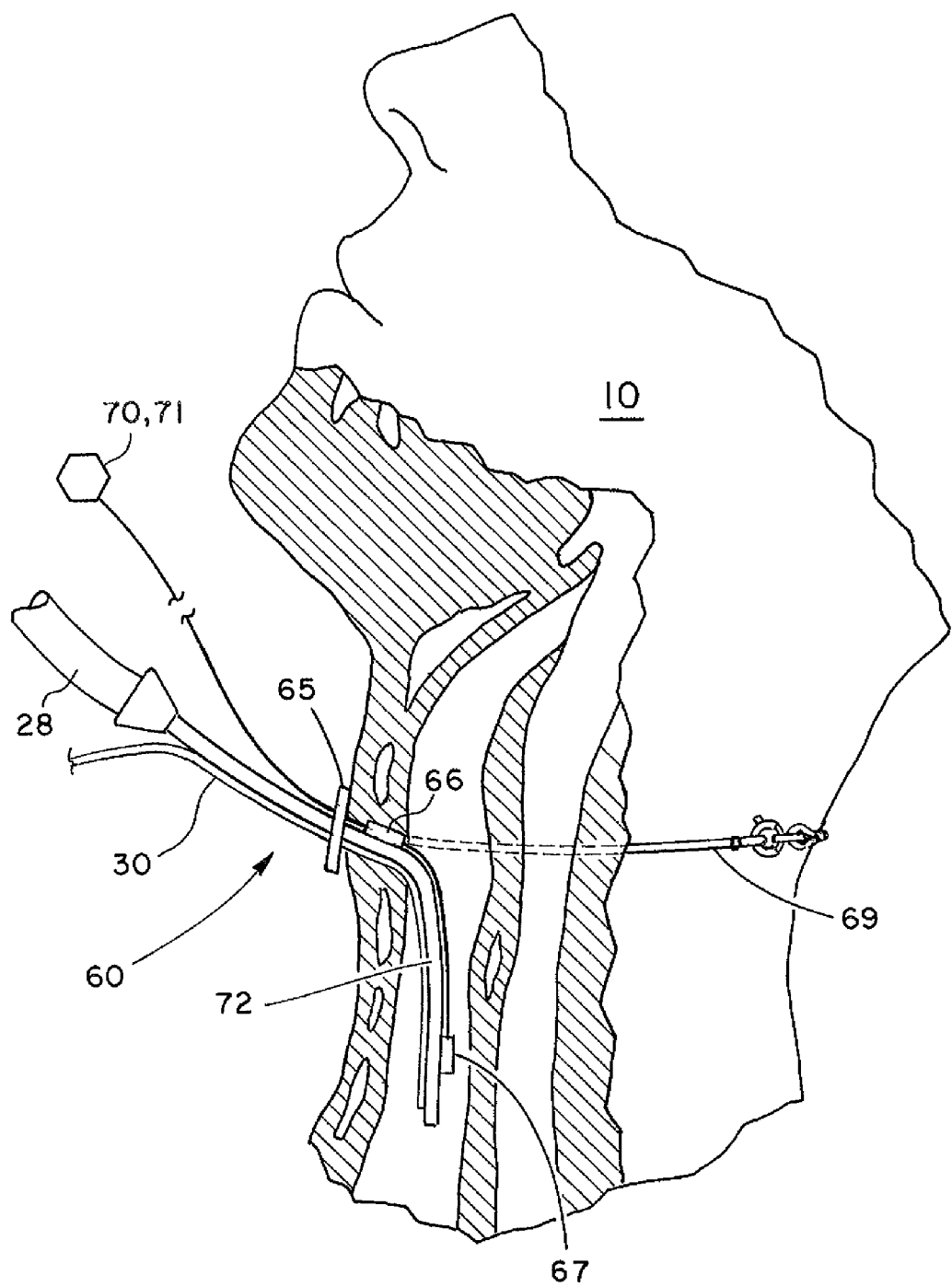
FIG. 7 is a cross-sectional view of a portion of a patient's airway following insertion of the tracheal catheter assembly shown in FIG. 6.

FIGS. 6 and 7 show an embodiment in which the airway interface tube 60 is a tracheal catheter assembly. FIG. 6 is a cross-sectional view of the tracheal catheter assembly. FIG. 7 is a cross-sectional view of a portion of a patient's airway 10 following insertion of the tracheal catheter assembly. The diameter of the tracheal catheter 72 should be selected to provide an adequate flow of oxygen-containing gas to achieve physiologic benefits such as significantly mitigating the airway pressure the patient must generate during spontaneous breathing and thereby reduce the patient's work of breathing. However, the diameter of the tracheal catheter 72 should be sufficiently small so as not to substantially interfere with the patient's spontaneous respiration around the tracheal catheter. The distal portion of the tracheal catheter 72 can be equipped with a variety of sensors (e.g., a thermistor 67) for sensing selected physical properties associated with the patient's respiratory cycle. Additionally, a sensor such as an oximeter sensor 66 placed adjacent to tissue in the neck, as illustrated in FIG. 7, can measure the patient's blood oxygen level similar to pulse oximetry. Sensors can be placed in any desired position or orientation with respect to the catheter 72 and are connected by sensor lines and connector 70, 71. In addition, one or more sampling tubes 30 extending along the tracheal catheter 72 enables sensors in the ventilation system 20 to monitor physical properties associated with the patient's respiration in the airway. The tracheal catheter 72 is held in place relative to the patient's trachea by means of a flange 65 and securing necklace 69 extending around the patient's neck.

Figure 8:
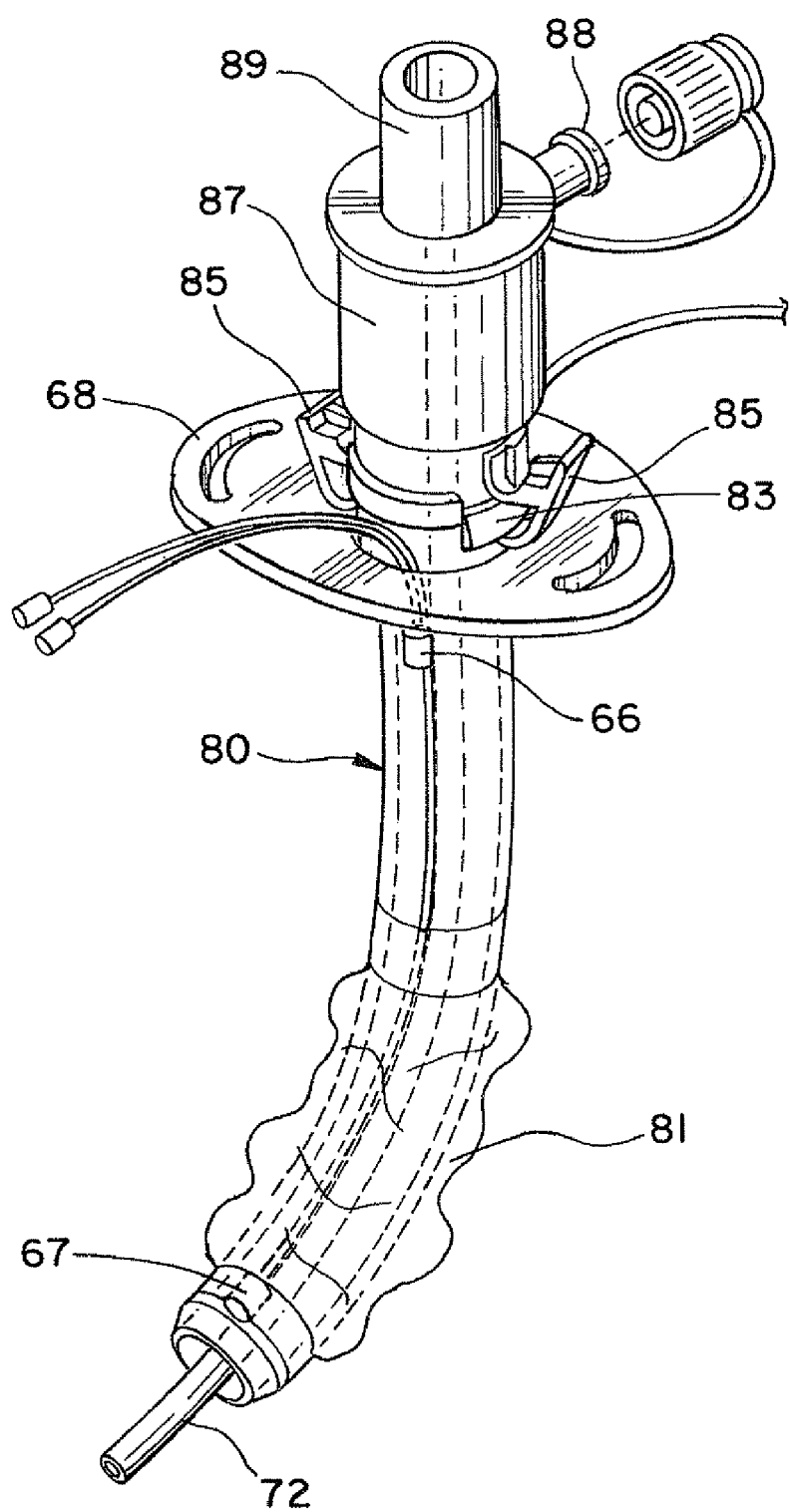
FIG. 8 is a perspective view of an embodiment of the airway interface 60 in which a tracheal catheter is assembled with a tracheostomy tube.
Figure 9:
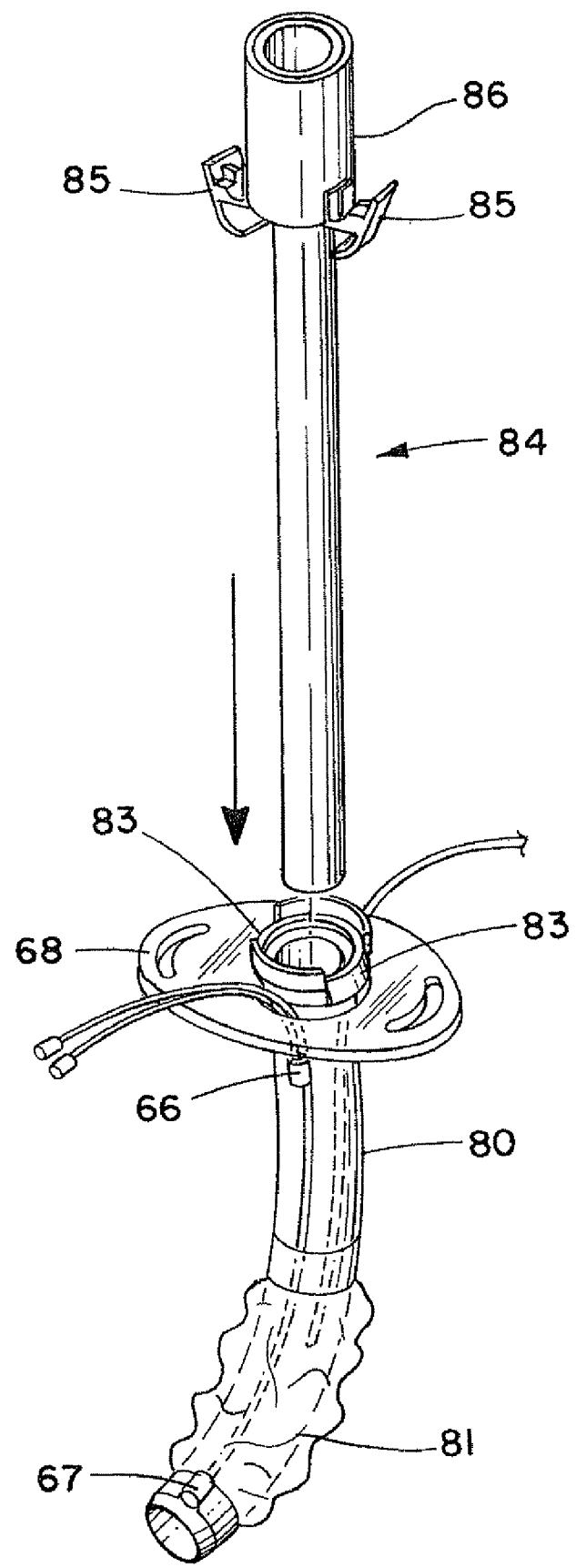
FIG. 9 is an exploded perspective view of the tracheostomy tube being assembled with its inner cannula.

FIGS. 8-12 show an embodiment of the airway interface 60 in which a tracheal catheter 72 is inserted through a tracheostomy tube 80. FIG. 8 is a perspective view of the assembly of the tracheostomy tube 80 as a modification of a conventional SHILEY™ tracheostomy tube marketed by Tyco Healthcare Group LP, Nellcor Puritan Bennet Division, of Pleasanton, California. The tracheostomy tube 80 has an insertable inner cannula 84 with a 15 mm connector 86 on its proximal end to allow attachment to a standard ventilator. The inner cannula 84 also has two securing grips 85 that engage ridges 83 on the proximal end of the tracheostomy tube 80 to removably secure the inner cannula 84 to the tracheostomy tube 80. FIG. 9 is an exploded perspective view of the inner cannula 84 being inserted through the tracheostomy tube 80. It should be noted that the tracheostomy tube 80 with its inner cannula 84 can continue to be used in the conventional manner, if desired, to ventilate the patient with a CSPPV ventilator. In this mode, the inflatable cuff 81 at the distal end of the tracheostomy tube can be inflated by means of a pilot balloon 82 to occlude the patients' trachea.

Figure 10:
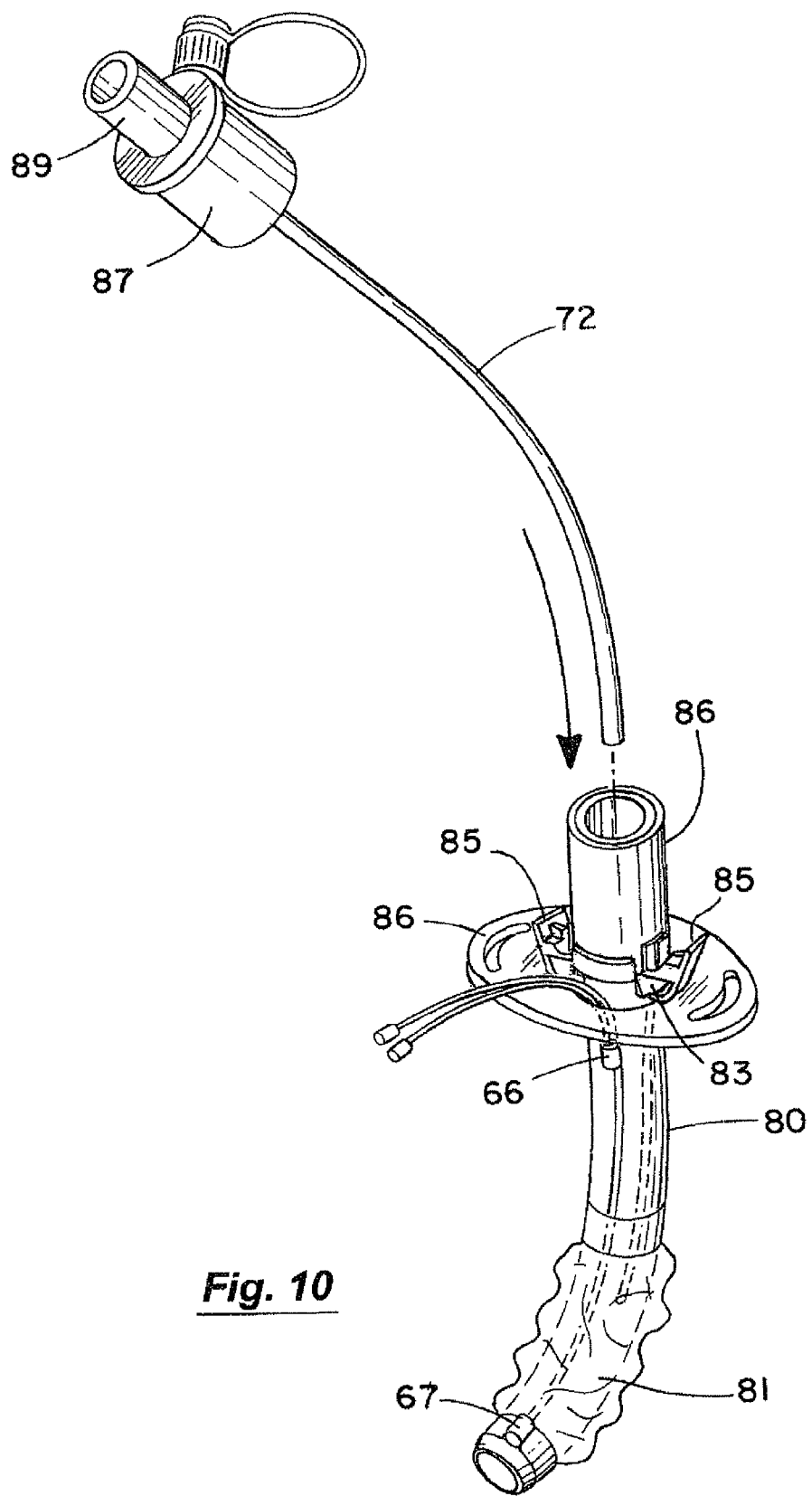
FIG. 10 is an exploded perspective view of the tracheal catheter being assembled with the tracheostomy tube and inner cannula.
Figure 11:
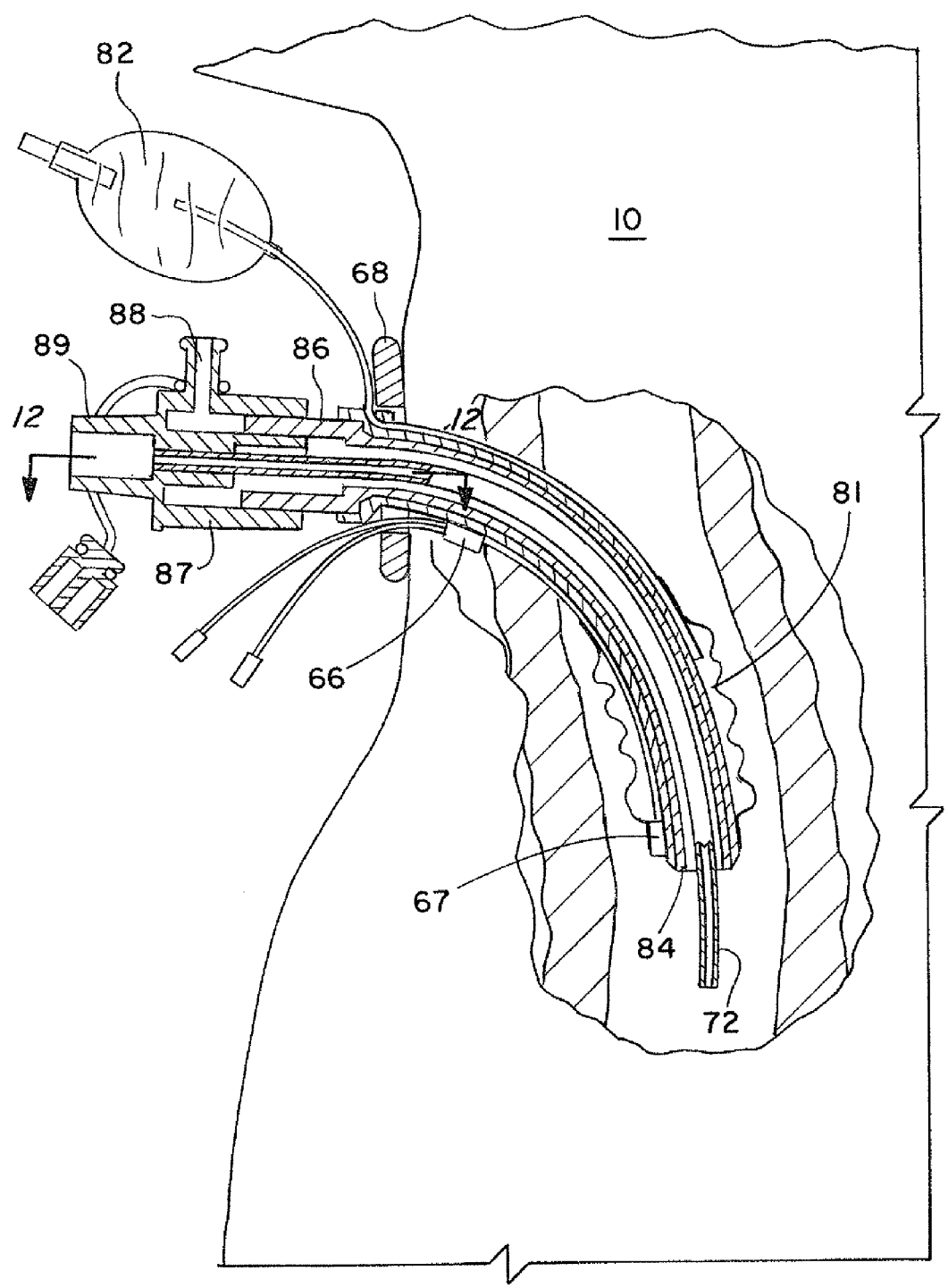
FIG. 11 is a vertical cross-sectional view of a patient's airway following insertion of the tracheostomy tube assembly shown in FIG. 8.

However, the embodiment of the airway interface 60 shown in FIGS. 8-12 also enables the present invention to be retrofit to a tracheostomy tube to provide a second mode of ventilation as an alternative to CSPPV. To illustrate this second mode, which is the subject of this invention, FIG. 10 is an exploded perspective view the tracheal catheter 72 being inserted through the tracheostomy tube 80 and its inner cannula 84. FIG. 11 is a vertical cross-sectional view of a patient's airway following insertion of the tracheostomy tube assembly shown in FIG. 8, with the cuff 81 deflated so as not to substantially interfere with the patient's spontaneous respiration around the tracheostomy tube 80.

Figure 12:
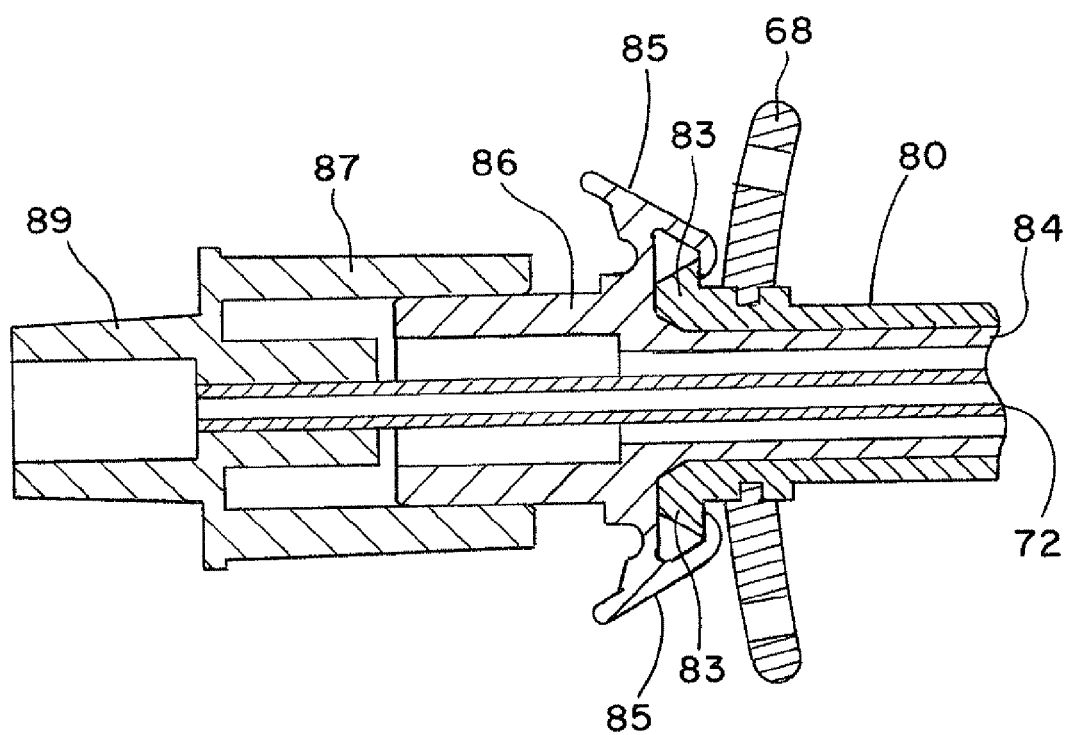
FIG. 12 is a detailed horizontal cross-sectional view of the connector portion of the tracheostomy tube assembly in FIG. 8.

The cap 87 on the proximal end of the tracheal catheter 72 fits over the connector 86 on the end of the inner cannula 84 of the tracheostomy tube 80. The cap 87 also includes an 11 mm connector 89 for attachment to the mid-section hose 28 (illustrated in FIGS. 1-5) leading from the ventilator system 20 in the present system. The outside diameter of the tracheal catheter 72 is typically much less than the inside diameter of the inner cannula 84 of the tracheostomy tube 80. This enables the pressure in the patient's airway to be monitored by the ventilator system 20 via a sampling tube connected to a pressure monitoring port 88 in the cap 87. FIG. 12 is a detail horizontal cross-sectional view of the connector portion of the tracheostomy tube assembly in FIG. 8.

The tracheostomy tube in FIGS. 8-11 is modified for the present system with a gas sampling tubing 67 extending along a portion of the tube. Additionally, an oximetry sensor 66 is attached to a portion of the tracheostomy tube. A variety of the other types and combinations of sensors and additional gas sampling tubings may be used. Alternatively, the tracheostomy tube and inner cannula as illustrated in FIG. 9 may be employed as the airway interface 60 for the present system without combined use with the tracheal catheter. The cuff is deflated and the 15 mm connector 86 on the inner cannula 84 is attached to a 15 mm connector on a mid-section hose 28 or directly to the heated circuit inspiratory limb 27 illustrated in FIGS. 1-5 equipped with a 15 mm interface connector. The present system can also be used with fenestrations (not shown) placed in the tracheostomy tube and inner cannula illustrated in FIGS. 8-11. Other tracheostomy tube designs modified with one or more sensors can also be used with the present system. Additionally, other tracheostomy tube designs modified with one or more gas sampling tubings can be used with the present system.

Figure 13:
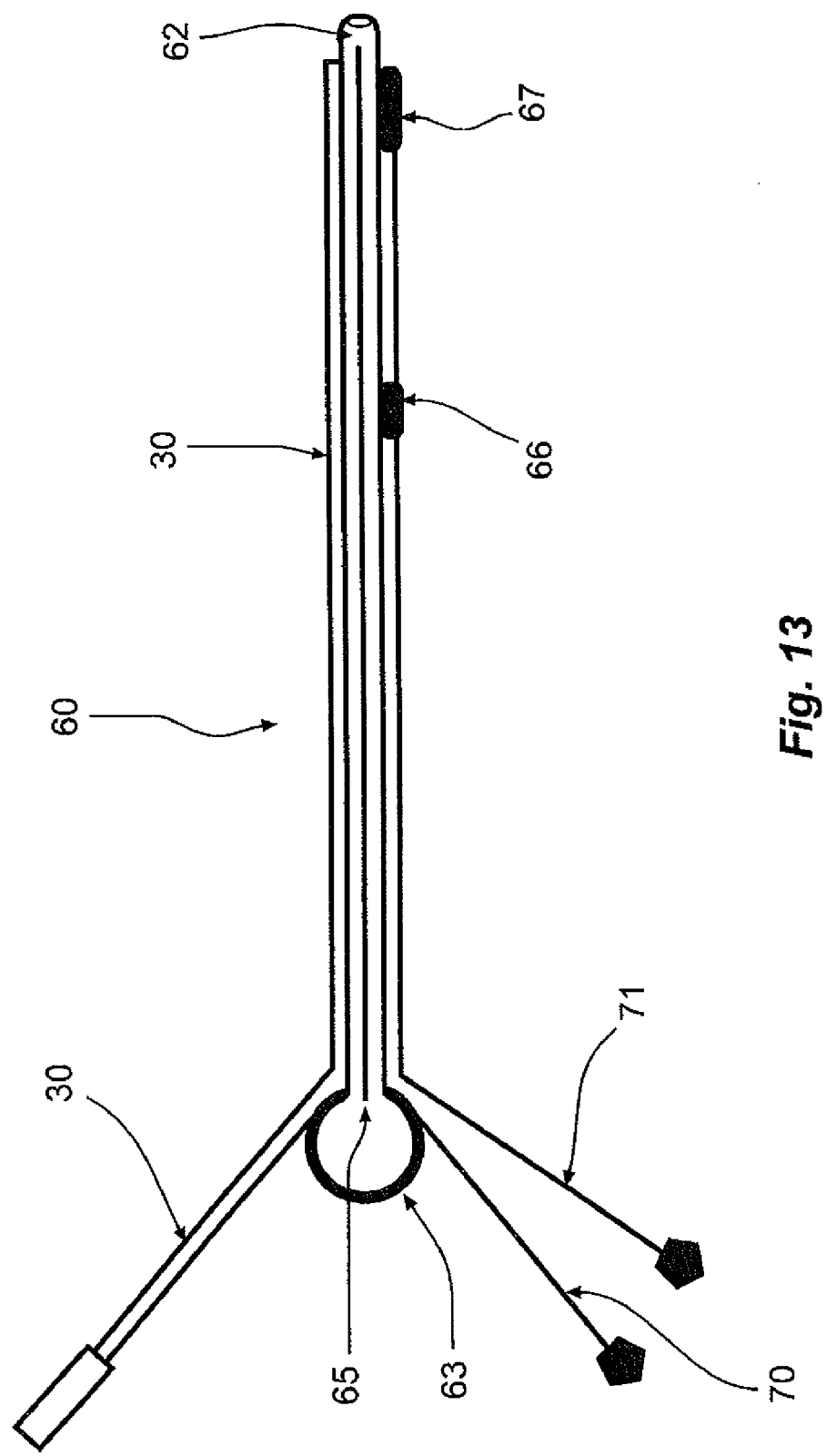
FIG. 13 is a cross-sectional view of an embodiment of the airway interface 60 intended for use as a nasopharyngeal catheter assembly.
Figure 14:
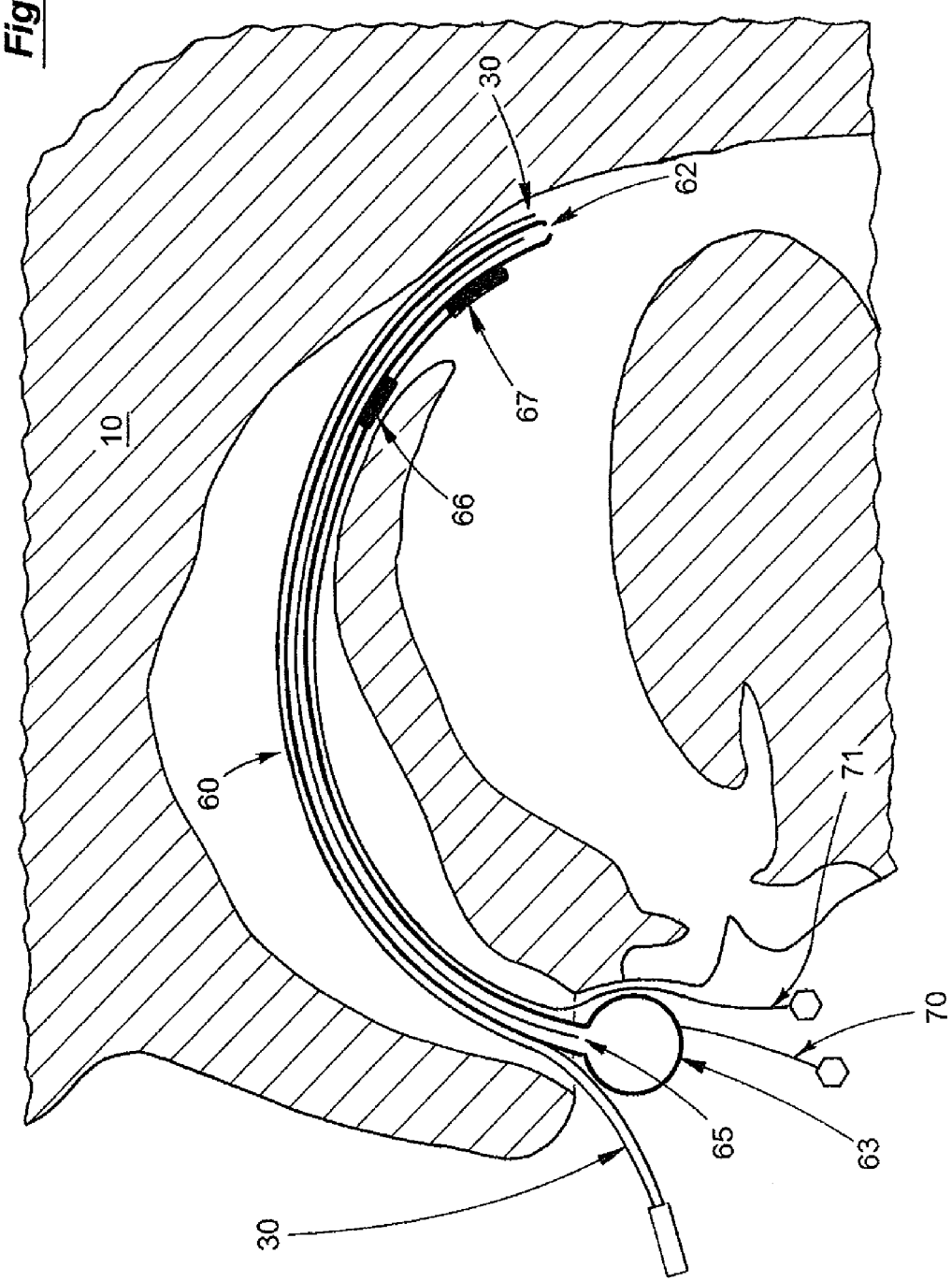
FIG. 14 is a cross-sectional view of a portion of a patients head following insertion of the nasopharyngeal catheter assembly shown in FIG. 13.
Figure 15:
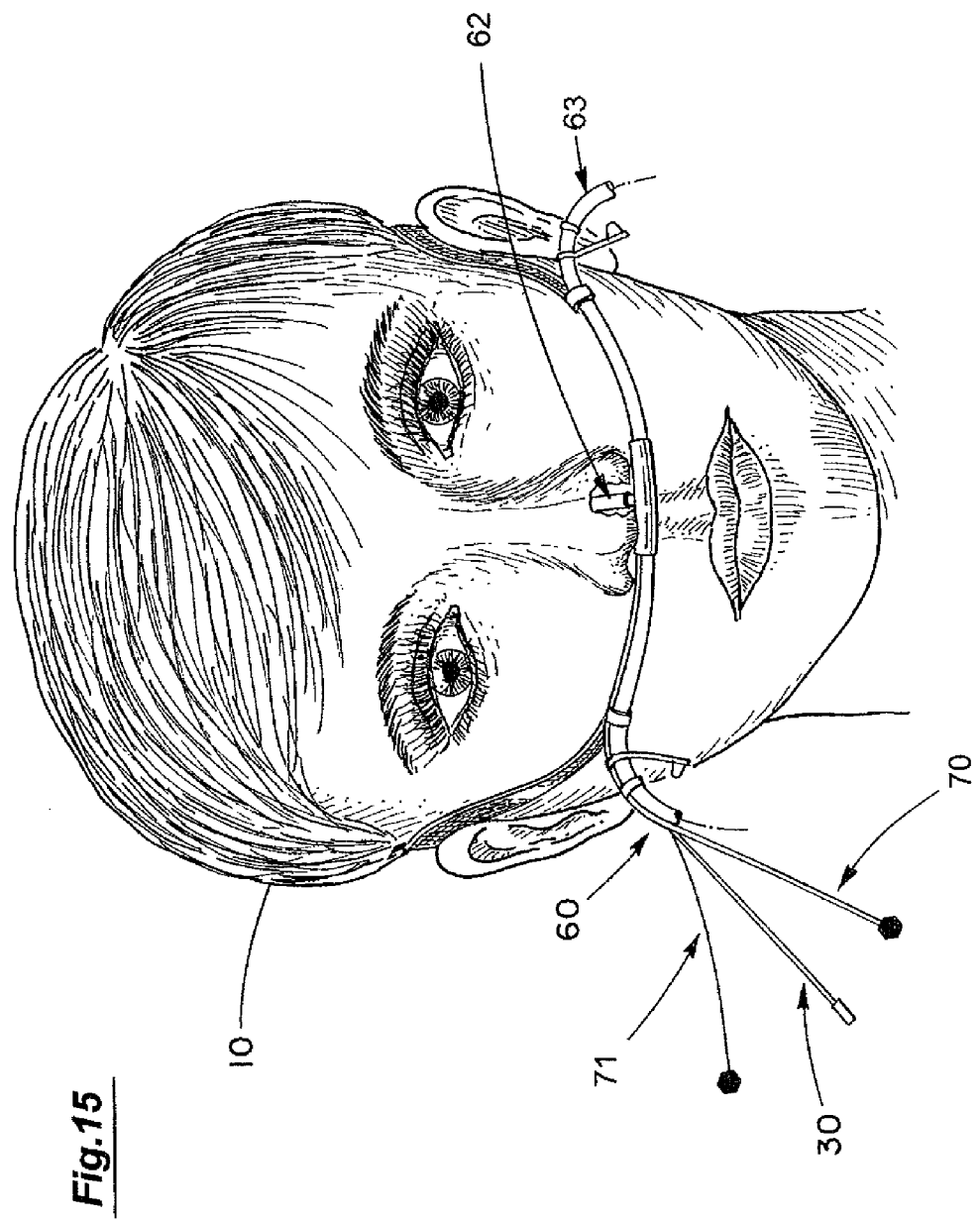
FIG. 15 is a front view of a patient's head following insertion of the nasopharyngeal catheter assembly in FIGS. 13 and 14.

FIGS. 13-15 show an embodiment of an airway interface 60 intended for use as an nasal tube, such as a nasopharyngeal catheter assembly. FIG. 13 is a cross-sectional view of a nasopharyngeal catheter assembly. In this embodiment, the airway interface 60 includes a nasopharyngeal catheter 62 designed for insertion through a patient's nostril into the nasopharynx as shown for example in the cross-sectional view provided in FIG. 14. In this embodiment, the tip of the catheter extends into the oropharynx, but could terminate in the nasopharynx. FIG. 15 is a front view of a patient's head following insertion of the nasopharyngeal catheter assembly. The catheter 62 includes a radio-opaque stripe 65 to guide insertion with x-ray imaging. Following insertion, a flow of oxygen-containing gas is supplied through the nasopharyngeal catheter 62 via connecting tubing 63 extending beneath the patient's nose at a flow rate sufficient to significantly mitigate the airway pressure the patient must generate during spontaneous breathing and thereby reduce the patient's work of breathing. The diameter of the catheter 62 is of lesser concern since it does not interfere with spontaneous breathing through the mouth. A thermistor 67 on a distal portion of the catheter can be used to monitor air flow in the pharyngeal airway. Electrical leads 71 run from the thermistor 67 along the catheter 62 and connecting tubing 63 to the ventilator system 20 to enable the processor 21 to synchronize the delivered flow of oxygen-containing gas to the patient's respiratory cycle. The embodiment of the airway interface 60 shown in FIGS. 13-15 also includes a pressure monitoring/gas sampling tube 30 as a second lumen parallel to the nasopharyngeal catheter 62. Optionally, an oximeter 66 on a distal portion of the catheter 62 contacts the mucosal tissue on the nasal cavity, as shown in FIG. 14, to monitor the patient's blood oxygen saturation. It should be noted that other types of nasal tubes could be substituted in place of a nasopharyngeal catheter.

Figure 16:
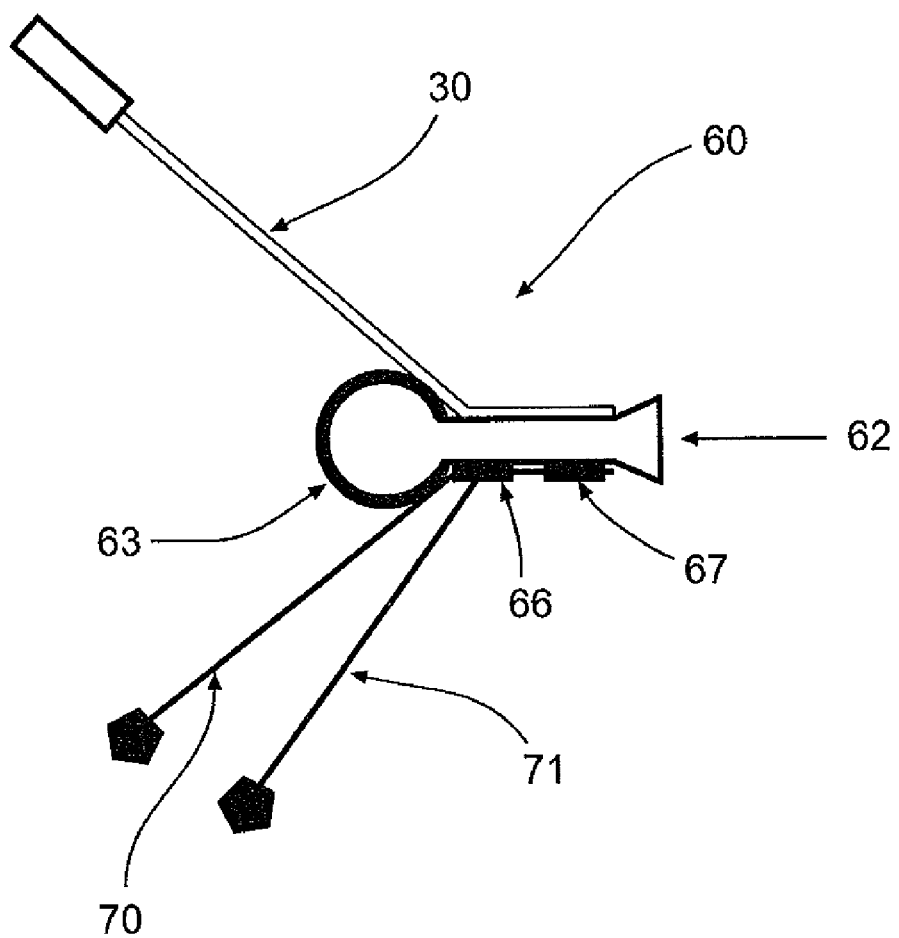
FIG. 16 is a cross-sectional view of an embodiment of the airway interface 60 intended for use as a nasal cannula assembly.
Figure 17:
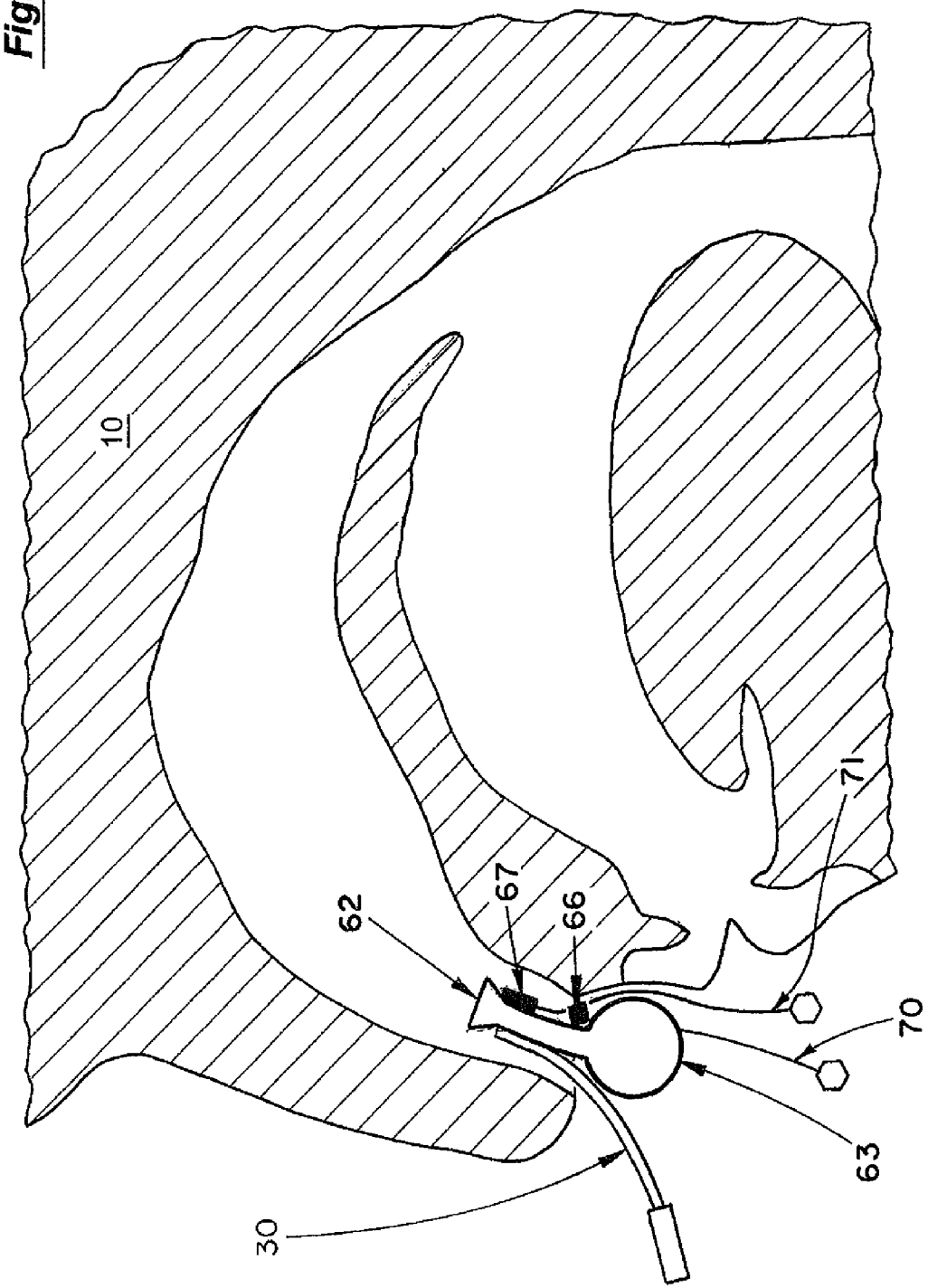
FIG. 17 is a cross-sectional view of a portion of a patients head following insertion of the nasal cannula assembly shown in FIG. 16.
Figure 18:
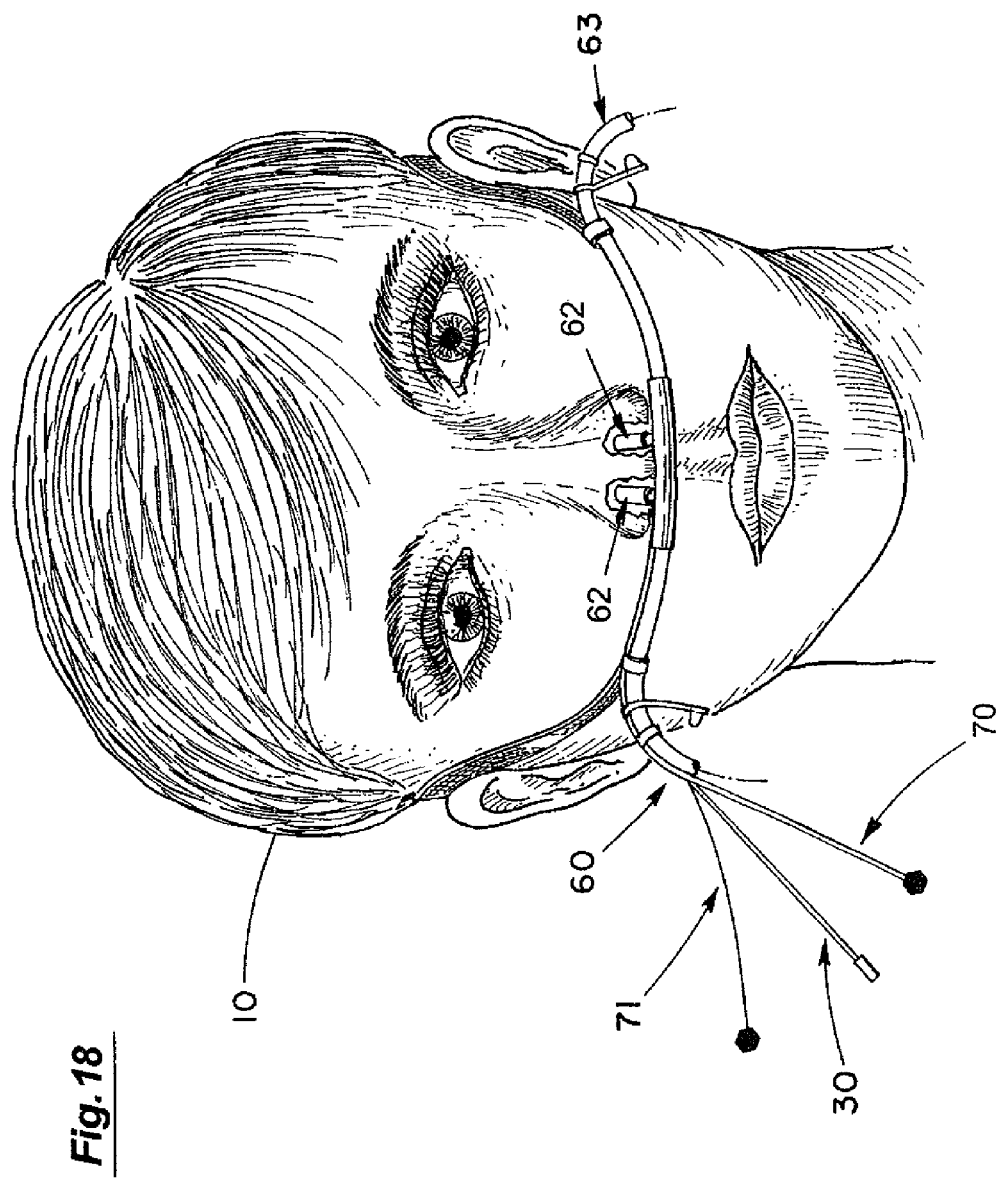
FIG. 18 is a front view of a patient's head following insertion of the nasal cannula assembly in FIGS. 16 and 17.

FIGS. 16-18 show another embodiment in which the airway interface 60 is a nasal cannula assembly. This embodiment is similar to that shown in FIGS. 13-15, but employs two shorter nasal cannulae 62 as the nasal tubes, in place of a single, long nasopharyngeal catheter. Here again, a number of sensors (e.g., an oximeter 66 or thermistor 67) and pressure monitoring/gas sampling tubes can be placed on the nasal tubes 62 to monitor the patient's respiration.

Figure 19:
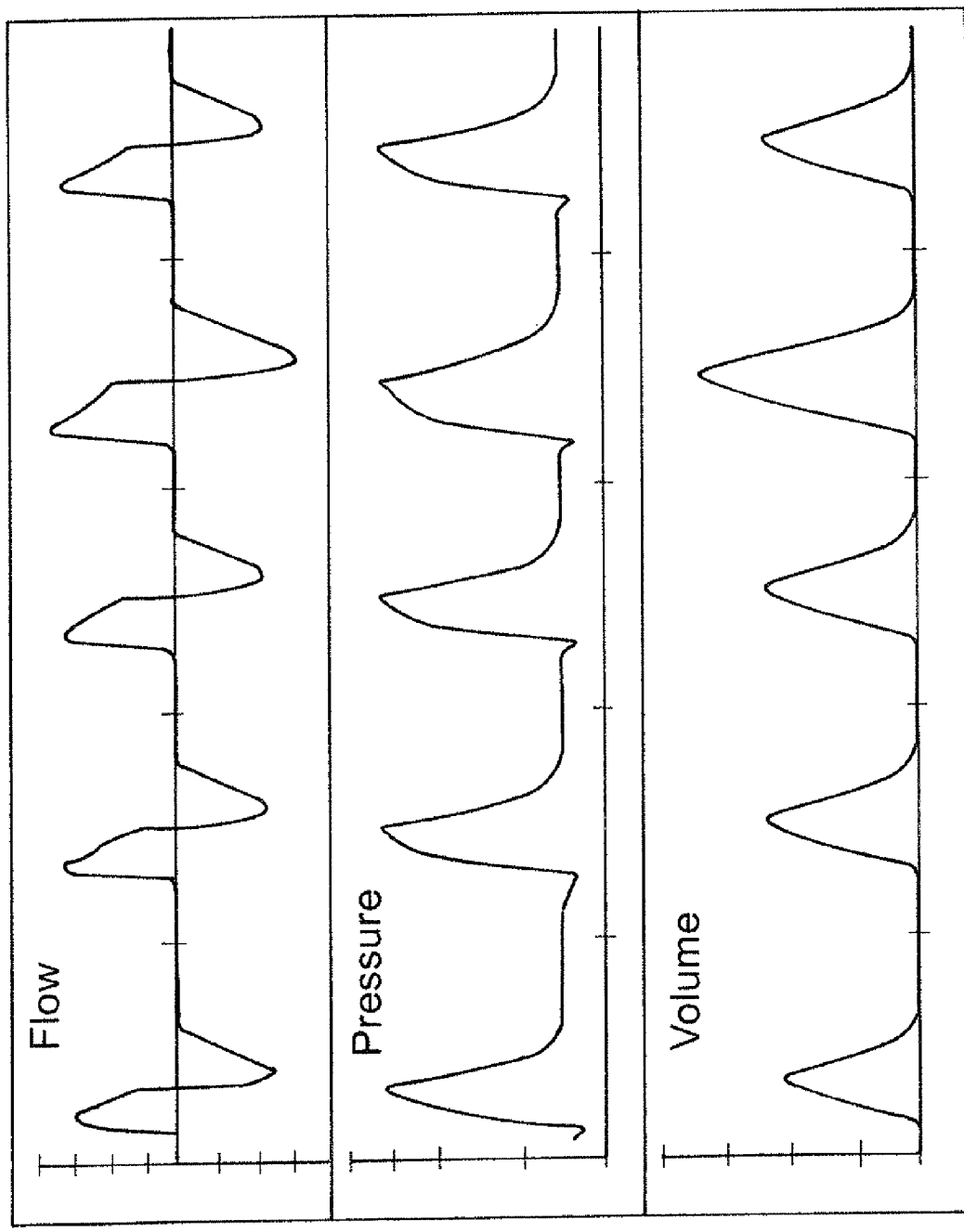
FIG. 19 is a set of graphs illustrating the respiratory mechanics with a prior art pressure-targeted CSPPV or SCSPPV.

Examples of Use. FIG. 19 illustrates pressure, flow and volume waveforms with breathing cycles experienced by a patient receiving prior art pressure-targeted CSPPV or SCSPPV. Time is on the horizontal axis. There are four phases to the respiratory cycle. There is a transition phase between expiration and inspiration, which is followed by the inspiratory phase. Similarly, there is a transition phase between inspiration and expiration which is followed by the expiratory phase. The inspiratory and expiratory phases also have different components. Prior art pressure-targeted CSPPV and SCSPPV devices and methods are designed to take over the patient's normal spontaneous negative pressure self-breathing. For example, in FIG. 19 this patient is receiving a commonly prescribed targeted pressure of 5 cm $H_2O$ during end expiration, or positive end-expiratory pressure (PEEP). During the beginning of the inspiratory phase, the patient makes an effort to spontaneously negative pressure breathe, which results in a transient drop in the applied positive pressure to approximately 3 cm $H_2O$, but not to a normal negative value. A series of pressure-targeted breaths are triggered each time the patient attempts to normally breathe, and the positive pressure ventilator will override the patient's natural efforts and will force, or pressurize the breath to exactly achieve the targeted maximal inspiratory pressure of 25 cm $H_2O$. Once the targeted pressure is reached, the exhalation valve opens and allows pressure to drop on exhalation, but the valve then closes when the targeted expiratory pressure of 5 cm $H_2O$ is reached. On a breath-by-breath basis, the maximum inspiratory flow and flow delivery patterns vary. A breath with a longer inspiratory time alters flow delivery and achieved tidal volume, even though targeted pressure is unchanged. Similarly, the maximum expiratory flows and flow patterns vary even though a targeted PEEP is achieved and maintained. Peak inspiratory flows and flow patterns are relatively independent of the target inspiratory pressure. Peak expiratory flows and flow patterns are relatively independent of the target expiratory pressure.

Figure 20:
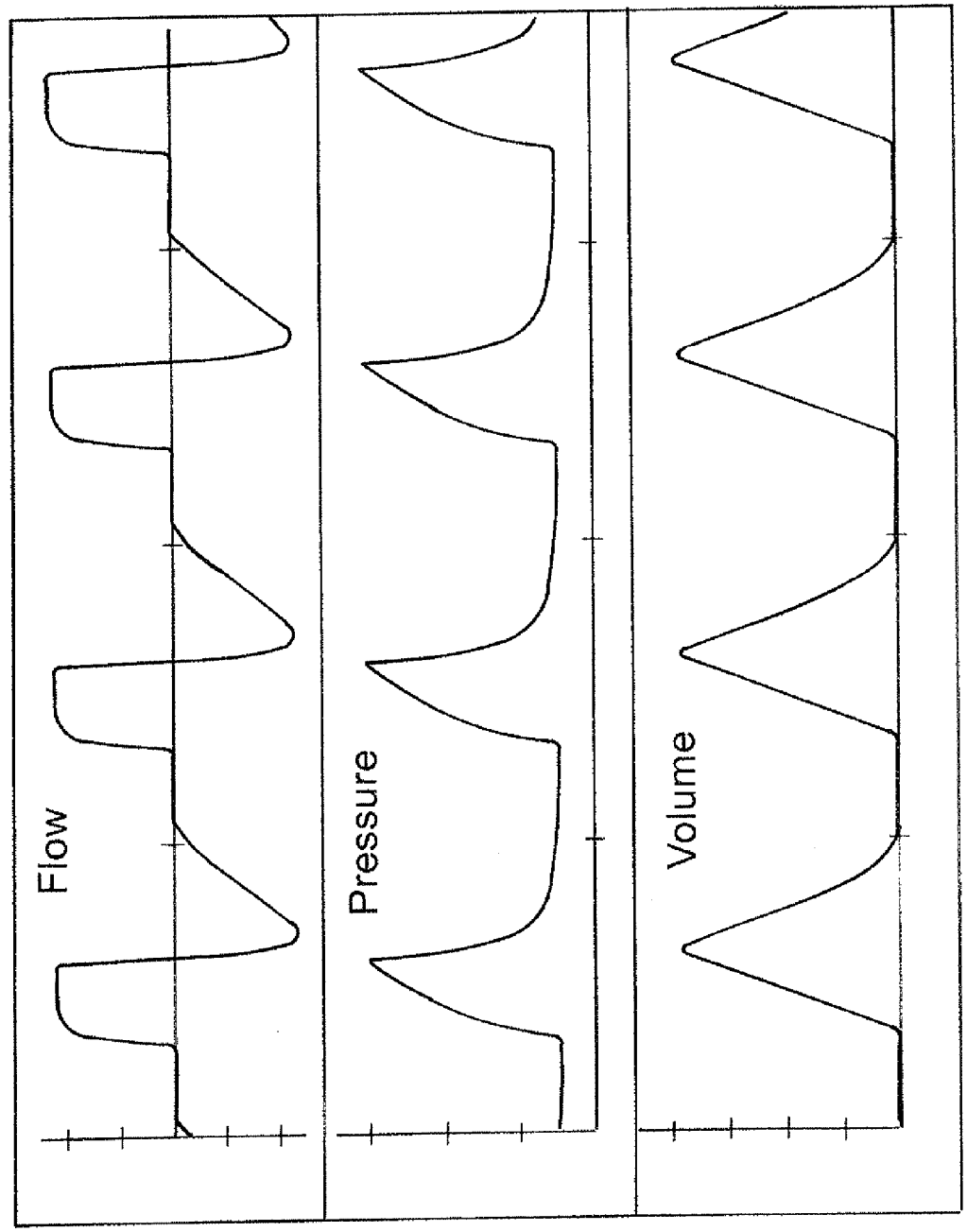
FIG. 20 is a set of graphs illustrating the respiratory mechanics with prior art volume-targeted CSPPV.

FIG. 20 illustrates implementation of a prior art volume-targeted CSPPV. The ventilator has a targeted tidal volume of 800 ml which is achieved with each breath. With a closed system and the mechanical properties of this patient's lungs (resistance, compliance, etc.) delivery of the targeted volume results in generation of 30 cm $H_2O$ at peak inspiration, and the pressure dissipates only when the exhalation valve opens allowing the patient to exhale. In addition to the targeted inspired volume, there is a commonly used expiratory targeted pressure, which is 5 cm $H_2O$ of PEEP that is maintained by closure of the expiratory valve. The patient is not making any efforts to self-breathe, and negative pressure deflections below the PEEP level are not seen. Consequently, because of the closed system and absence of self-breathing, the targeted volume is achieved with each breath and no variations in pressure, flow or flow patterns are seen in this steady state. Had self-breathing efforts occurred with volume-targeted CSPPV, variability in peak pressure and both peak flow and flow patterns would have been observed.

Figure 21:
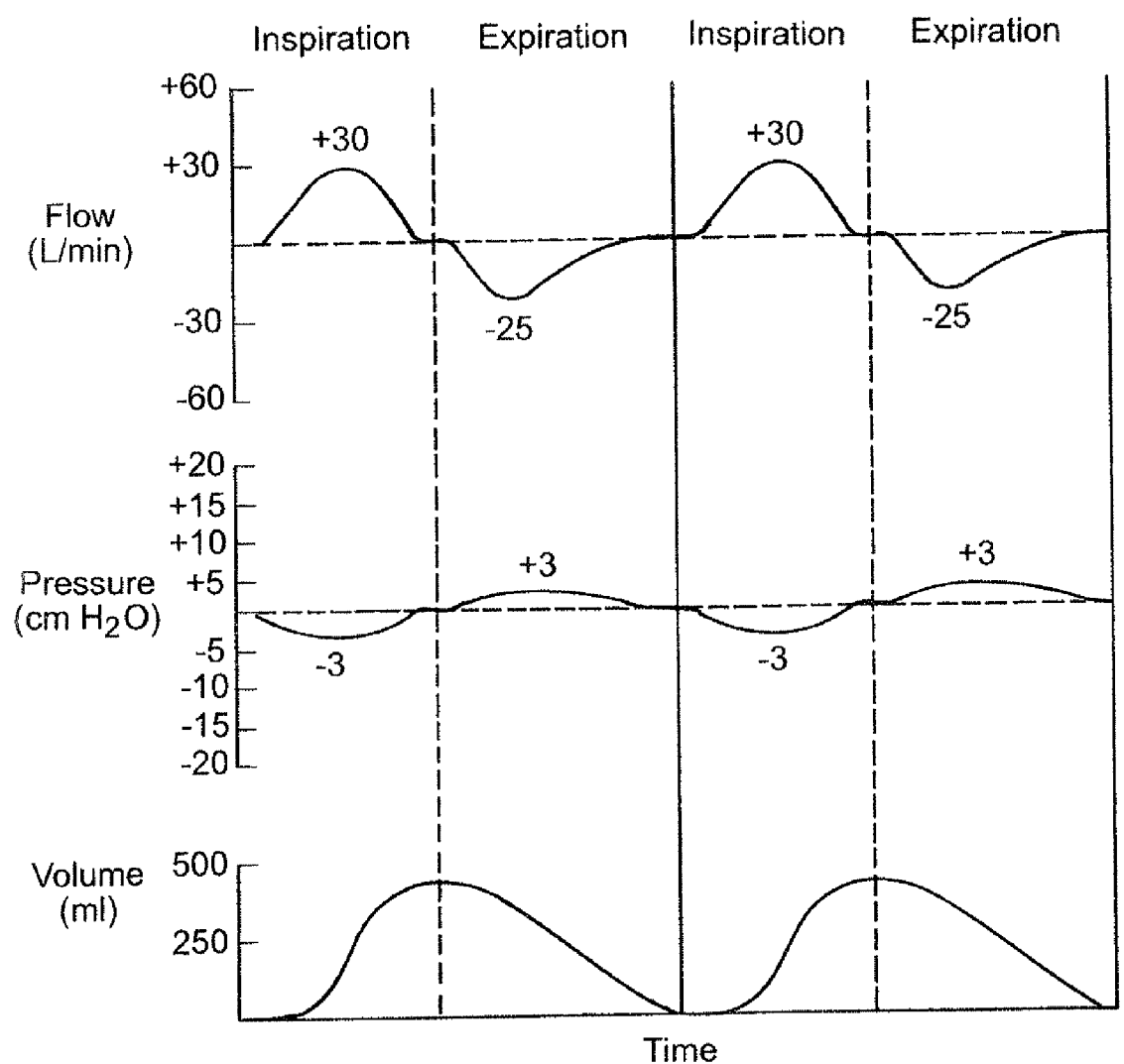
FIG. 21 is a set of graphs illustrating the respiratory mechanics in a normal healthy person in a relaxed state.

FIG. 21 illustrates respiratory mechanics in a normal negative-pressure self-breathing healthy person in a relaxed state. This is representative of how individuals spontaneously breathe when independent from either a positive pressure or negative pressure mechanical ventilator. In short, individuals self-generate a negative or sub-atmospheric pressure that draws the breath into the lungs. During the inspiratory phase, the person uses respiratory muscles to generate negative pressure. Since the lungs are healthy, minimal work of breathing (WOB) is required to draw adequate flow into the lungs. At about mid-inspiration the amount of negative pressure as well as flow into the lungs has reached the peak, and values begin to return to the baseline of zero pressure and flow (sinusoidal pattern). During the transition phase between inspiration and expiration there is a slight pause where negative pressure has dissipated, inspiratory flow has ceased and no additional volume has entered the lungs. During the exhalation phase, the elastic recoil of the lungs and chest wall is enough to cause the gas flow to carry the inspired volume out of the lungs and into the atmosphere under negligible resistance. Minimal positive pressure is generated and little or no expiratory WOB is done. Again, expiratory pressure and flow occur in a sinusoidal pattern. There is also a brief period of zero pressure and zero flow in the transition phase between expiration and inspiration where no volume exchange occurs. The ratio of inspiration to expiration is approximately 1:1.5, which is an efficient pattern that maintains a normal respiratory rate and adequate time for exhalation with normal lungs.

Figure 22:
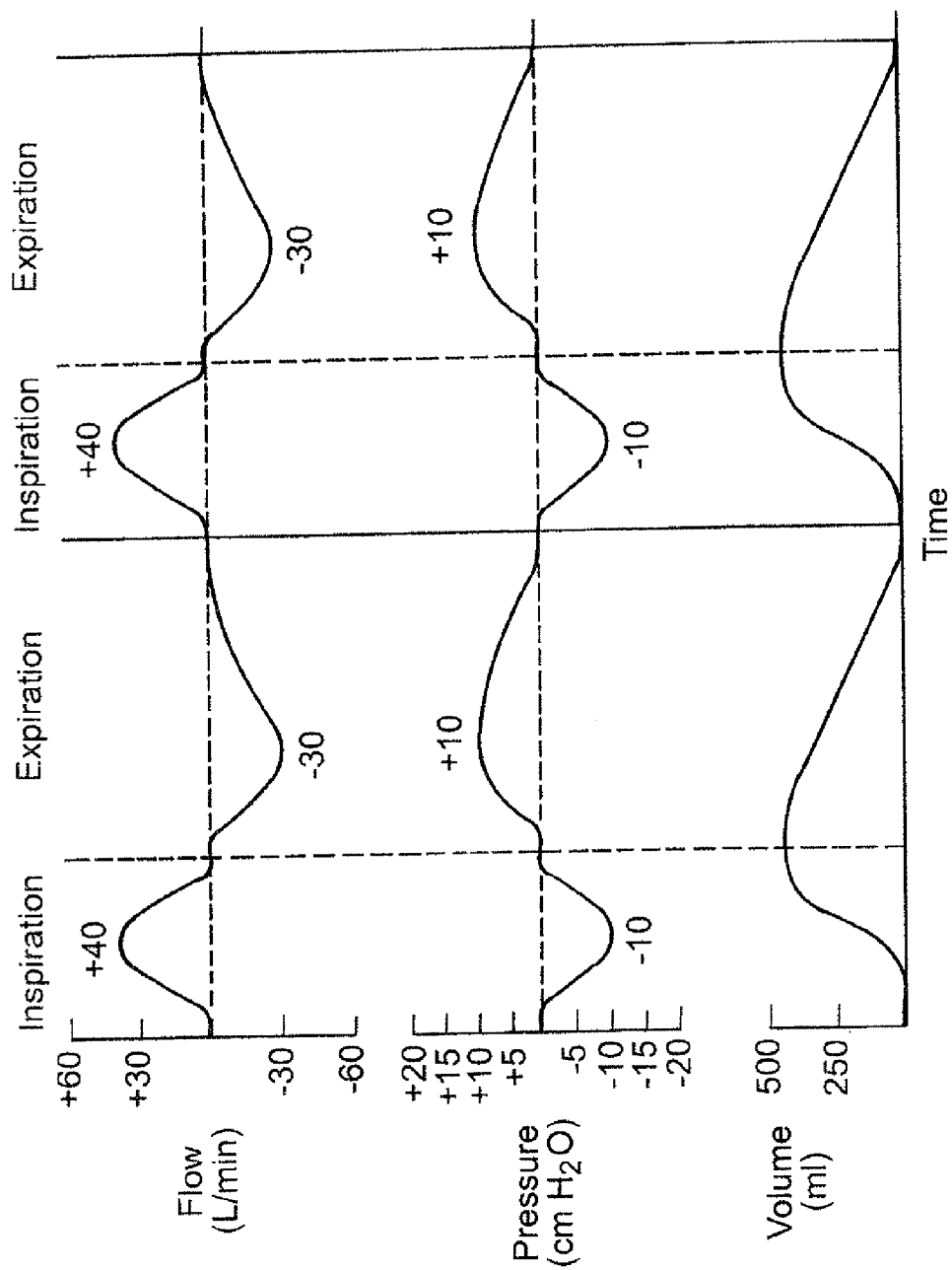
FIG. 22 is a set of graphs showing the respiratory mechanics in a patient in respiratory distress due to an exacerbation of emphysema with bronchitis.
Figure 23:
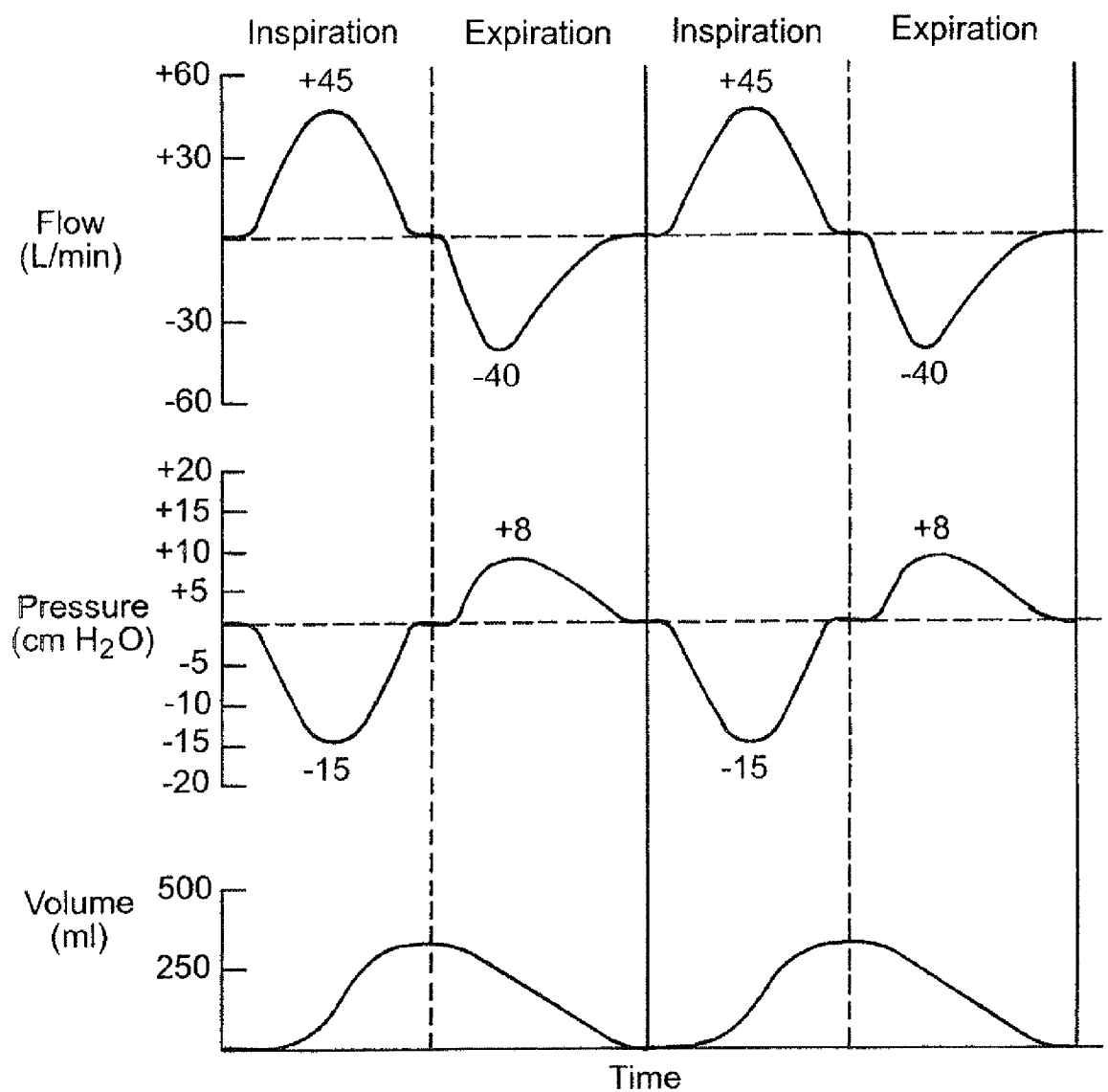
FIG. 23 is a set of graphs showing the respiratory mechanics for a patient with Adult Respiratory Distress Syndrome (ARDS).
Figure 24:
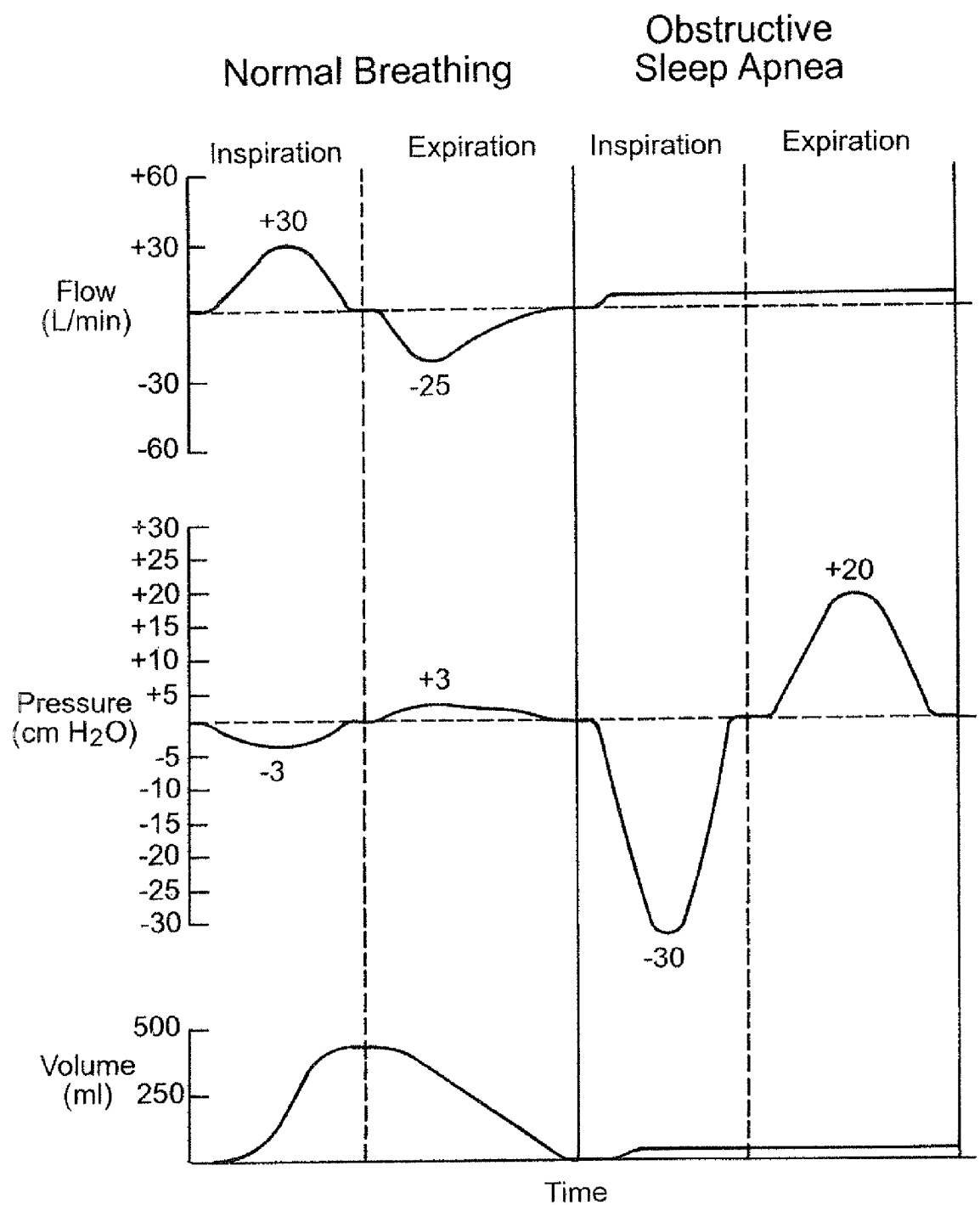
FIG. 24 is a set of graphs showing the respiratory mechanics for a patient with obstructive sleep apnea with respiratory distress.

The following discussions and accompanying FIGS. 22-24 present examples of pathophysiology of a number of diseases and disorders that may benefit from use of the present invention. Application of the invention is by no means limited to these examples of diseases and disorders.

FIG. 22 shows contrasting respiratory mechanics in a self-breathing patient in respiratory distress due to an exacerbation of emphysema with bronchitis. Increased airway resistance resulting from bronchial airway obstruction directly increases inspiratory WOB. The over-distended diseased lung is difficult to inflate and inspiratory WOB is increased. Consequently, the airway pressure curve swings significantly more negative throughout the sinusoidal inspiratory phase, due to increased inspiratory WOB. Patients have difficulty drawing the breath down into the deep alveolar regions of the lungs where oxygen uptake occurs. Since the respiratory muscles in emphysema patients do not perform normally, there is a limit to how much extra work can be performed. Though pressure may transiently return to zero during the phase between inspiration and expiration, the airways are so collapsed and obstructed that significant expiratory WOB is required to allow the trapped breath to be exhaled. Patients purse their lips and close their vocal cords (which do not require much energy) and then forcefully engage their expiratory respiratory muscles to build up back-pressure required to mechanically dilate the airways so that obstruction can be improved and exhalation can more effectively occur in this disease state. Consequently, expiratory pressures are elevated even during normal negative pressure breathing that occurs without positive pressure mechanical ventilation. The patient also tries to allow more time for trapped gas to be exhaled, so even though the time required for inspiration is little changed, proportionately more time is spent in exhalation (1:2 ratio). This requires a slower respiratory rate. If this can not occur, air trapping (hyperinflation) results. This inefficient breathing pattern causes worsening gas exchange and mechanics and further increases in WOB.

In addition to requirements for increased inspiratory and expiratory WOB, other physiologic derangements in patients with emphysema are hypoxemia, increased physiologic dead space and reduced alveolar ventilation. Destruction of the alveoli (air sacs) and related blood vasculature and airway disease impair the effectiveness and efficiency of gas exchange, resulting in reduced uptake of oxygen and elimination of carbon dioxide. Due to the disease, patients have mismatch where the areas of ventilation don't adequately match blood flow, so inadequate oxygen enters the body (hypoxemia). Additionally, there are many bronchial tubes that lead to diseased alveolar sacs where there is ventilation, but completely inadequate blood flow. Consequently, ventilation is wasted and there is increased dead space due to completely inadequate gas exchange. Consequently, for a given tidal breath in, a higher than normal portion of it does not get to the alveolar sacs where oxygen can be taken up and carbon dioxide can be released from the blood stream (inadequate alveolar ventilation). Additionally, during the last component of the expiratory phase, some of the carbon dioxide does not get exhaled into the atmosphere and is trapped in the airways (trachea, bronchial tubes, pharynx, oral and nasal cavity) and alveolar sacs without blood flow (physiologic dead space). Patients with increased physiologic dead space, as in this example, have more trapped carbon dioxide that is breathed in to the alveolar sacs again during the first component of the next inspiratory phase. The self-breathing patient has few choices; either increase the respiratory rate and/or tidal volume in an effort to try to get more minute ventilation to functioning alveolar sacs (this requires an even further increase in WOB), or to give in to excessive WOB and retain carbon dioxide in the blood (develop worsening respiratory acidosis, or respiratory failure). The present system is uniquely positioned to improve or correct these physiologic abnormalities while still allowing the patient to spontaneously self-breathe without CSPPV or SCSPPV. This presentation of a patient with respiratory distress due to an exacerbation of emphysema is intended to illustrate one end of the spectrum of respiratory compromise with one example of a disorder where specific physiologic abnormalities occur and can be tied to a specific phase or component of a phase in the self-breathing cycle.

Negative-pressure self-breathing in a neurologic or neuromuscular disease patient with respiratory distress should also be considered. Patients with spine or brain injury and those with neuromuscular disorders can have significant respiratory distress due to impaired neurologic respiratory drive to breathe or due to the fact that the respiratory muscles are unable to generate adequate WOB. The respiratory mechanics would have a similar pattern to the healthy person in FIG. 21 except that adequate negative pressures may not be sustained during negative pressure self-breathing. Consequently, air flow and the tidal volume decrease. The low tidal volume results in a high dead space to tidal volume ratio, and functioning alveolar sacs receive inadequate alveolar ventilation. Elevated carbon dioxide and low blood oxygen levels can result. Mismatches in blood flow and gas in alveolar sacs can further compromise blood oxygen levels. The present invention is uniquely positioned to improve or correct these physiologic abnormalities while minimizing required WOB and still allowing the patient to spontaneously self-breathe without CSPPV or SCSPPV.

FIG. 23 illustrates a patient on the other end of the spectrum of respiratory compromise with one example of a disorder called Adult Respiratory Distress Syndrome (ARDS). The self-breathing pattern is different than FIG. 21. The ARDS patient has some common features with the patient in FIG. 22, but also some very different pathophysiologic derangements. Unlike the over-stretched and poorly elastic lung in emphysema, ARDS causes a very stiff lung that is difficult to inflate and the lungs have blood flow that is shunted around alveolar sacs that are collapsed or full of fluid (congestive atelectasis). Consequently, very little oxygen gets to the lungs and the patient is driven to breathe deep and fast to attempt to get more oxygen into functional alveolar sacs to compensate. Though still inspiring with a normal sinusoidal negative pressure swing during the inspiratory phase of breathing, the negative pressure pattern is pronounced due to the high inspiratory WOB required to inflate the stiff lungs with the high ventilatory requirements. Any reduction in either anatomic or physiologic dead space would be beneficial in reducing excessive ventilatory requirements. Patients have difficulty drawing the breath down into the deep functioning alveolar regions of the lungs where oxygen uptake can occur. Intense WOB is required. Though the elastic recoil of the stiff lung helps gas initially escape during the early expiratory phase, expiratory WOB (particularly during the later segments of the expiratory phase) is increased to force the gas out of the lungs so the expiratory time can be shorter (1:1 ratio) allowing a faster respiratory rate without significant compromise of the relationship of inspiration to the total breathing cycle (respiratory duty cycle). Pressure also swings positive during the expiratory phase as patients have increased expiratory WOB in an effort to force flow during expiration into collapsed alveolar sacs (atelectasis) for lung recruitment. The inspiratory and expiratory WOB are further driven by the respiratory center's intense stimulus to drive higher tidal volumes and faster respiratory rates. The present invention is uniquely positioned to improve or correct these physiologic abnormalities while still allowing the patient to spontaneously self-breathe without CSPPV or SCSPPV.

FIG. 24 shows respiratory mechanics during negative-pressure self-breathing in a patient with obstructive sleep apnea with respiratory distress. A normal respiratory cycle during sleep where obstruction is not present is illustrated on the left. It is similar to FIG. 21. However, in an iterative cyclic fashion, the upper airway totally obstructs, resulting in the absence of inspiratory flow and absence of inspiratory volume. Large negative pressure values are generated as the patient struggles to inspire. Similarly, the patient forcefully attempts to exhale against the obstructed upper airway and significant expiratory pressures are generated, but flow is curtailed and there is no inspired tidal volume to exhale. The obstruction is aggravated because upper airway tissue is "sucked" together by the stronger and stronger negative pressure efforts and "obstruction begets obstruction" because nothing is stenting the opposing tissues to keep them apart as negative pressure efforts increase. Abnormalities in oxygen and carbon dioxide exchange occur and cardiovascular and neurologic impairment with severely disrupted sleep architecture are problematic.

Continuous Positive Airway Pressure (CPAP), which is a form of SCSPPV, uses pressure to prevent obstruction with sleep apnea patients and to prevent large negative pressure swings. Similarly, the present system is uniquely positioned to improve or correct these physiologic abnormalities while still allowing the patient to spontaneously self-breathe without the need for CPAP and associated discomforts and complications encountered with SCSPPV. Sleep apnea patients can have central episodes, where there are iterative periods throughout sleep where no efforts are made to breathe. Patients have breathing cycles with no upper airway obstruction, but the absence of flow, volume and pressure are noted. The problems are getting adequate oxygen deep into the alveolar units where oxygen uptake can occur and getting carbon dioxide expelled into the atmosphere. The present invention is uniquely positioned to improve or correct these physiologic abnormalities while still allowing the patient to spontaneously self-breathe without the need for CPAP and associated discomforts and complications encountered with SCSPPV.

The following discussions and FIGS. 25-32 serve to specifically demonstrate how using an open system to provide pressure-mitigating, breath-synchronized, flow-targeted ventilation can improve physiology in self-breathing patients with the previously described diseases and disorders. As stated previously, use of the invention is not limited to these disease and disorder examples. Furthermore, these example figures are not intended to limit the scope of the invention. It should be noted that the flow waveforms and associated flow rates of oxygen-containing gas delivered through the airway interface 60 should be sufficient to achieve the desired physiological benefit for the patient, such as reducing the patient's work of breathing by reducing the airway pressure that the patient must generate during spontaneous breathing, flushing carbon dioxide from the patient's airway, and increasing ventilation and improving blood oxygenation. This typically requires a peak flow rate in the approximate range of 7 to 60 L/min for adults, and proportionally reduced peak flow rates for pediatric and infant populations. The inspiratory and expiratory flow waveforms and related flow rates associated with phases of the inspiratory and expiratory respiratory cycle are examples only. Required flow rates and waveforms may change from time to time in the management of an individual. Similarly, required flow rates and waveforms will vary based upon the management of adult, child or infant populations.

Figure 25:
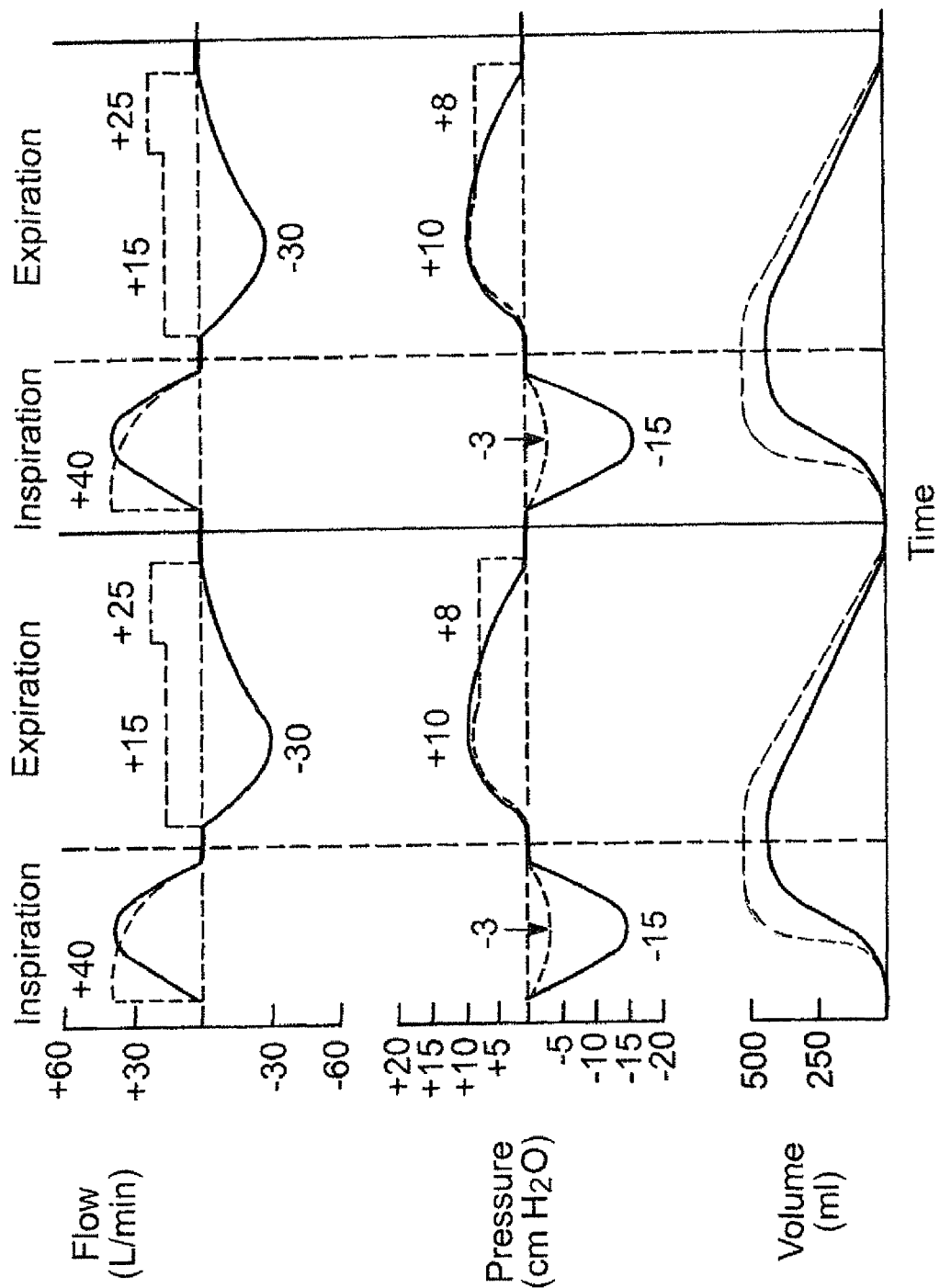
FIG. 25 is a set of graphs illustrating breathing in an emphysema patient in respiratory distress treated using the present invention to provide interrupted flow-targeted ventilation.

FIG. 25 illustrates negative-pressure self-breathing in an emphysema patient in respiratory distress treated using the present invention to provide interrupted flow-targeted ventilation (Example 1). FIG. 25 and others that follow show two respiratory cycles of the previous examples of impaired respiratory mechanics in patients with respiratory distress due to different respiratory disorders with specific pathophysiologic derangements that have been previously defined. A key element is that the present invention supports the normal self-breathing process while either eliminating or minimizing problems encountered with prior art systems.

As previously mentioned, there are four phases to the respiratory cycle. There is a transition phase between expiration and inspiration, which is followed by the inspiratory phase. Similarly, there is a transition phase between inspiration and expiration which is followed by the expiratory phase. Furthermore, there are components within the inspiratory and expiratory phases. The flow, pressure and volume generated with the patient's unsupported self-breathing in FIG. 25 are illustrated on the vertical axis in solid lines. Intervention with peak flows and flow patterns delivered by the invention that are superimposed upon the respiratory cycle of the self-breathing patient in an open system is demonstrated in dashed lines. Expected clinical response with respect to alterations of patient pressure patterns achieved as a result of superimposed targeted flows delivered by the invention is shown in dashed lines. Dashed lines also reflect the anticipated increases in tidal volume resulting from use of the invention. Other anticipated physiologic outcomes of the invention are discussed. In this particular example there is interrupted flow delivery in the transition between expiration and inspiration and between inspiration and expiration that matches a normal breathing pattern.

FIG. 25 shows a rapidly accelerating inspiratory flow with a peak of 40 cm $H_2O$. The initial accelerated flow is synchronized with the patient's initial inspiratory effort in the very first component of the inspiratory phase. The early onset of a high flow that exceeds the requirement of the normal breathing pattern facilitates delivery of gas deep into functional alveolar gas exchange units which results in improved alveolar ventilation and consequently improved oxygen uptake and carbon dioxide elimination. Flow during the very early component of the inspiratory phase has maximum impact upon oxygen delivery during self-breathing. Following the accelerated inspiratory flow during the early inspiratory phase, the pattern transforms into a convex decelerating pattern that overlays a sinusoidal flow pattern of the patient's breath during mid to late inspiration. The rapidly accelerating peak inspiratory flow (+40 L/min peak in FIG. 25) and flow pattern reduces inspiratory WOB because the device delivers flow on the leading edge of the breath and less respiratory muscular work is required to physically draw the gas into the lungs. The decelerating flow pattern superimposed upon the patient's diminishing flow supports the diminishing needs for work to be performed during the remainder of the inspiratory phase. The inspiratory flow supplied by the present system also enhances alveolar ventilation during this phase of the patient's respiratory cycle and tidal volume is increased.

FIG. 25 demonstrates a reduction in the inspiratory negative-pressure swing, which indicates reduced inspiratory WOB. In other words, the negative pressure required by the patient to inspire is mitigated by use of the device's targeted flow pattern. Because of the open design of the system, positive pressure during inspiration does not occur because any gas that is not inhaled can easily escape into the atmosphere, mitigating positive pressure buildup. At the onset of expiration, a flow of 15 L/min is triggered in this example and a rectangular flow pattern continues through early and mid exhalation. Patients with emphysema purse their lips and vocal cords throughout exhalation (which requires negligible work) and then use the work of the expiratory muscles to build up back-pressure to mechanically dilate diseased airways to facilitate exhalation. The expiratory flow and flow pattern delivered by the device mechanically dilates the diseased airways and mitigates the pressure that the patient would otherwise generate by increased WOB. During the late component of exhalation the peak flow with the rectangular flow pattern is increased to 25 L/min. This flow boost continues to further mechanically dilate the airways to prevent distal airway collapse, but also flushes out the carbon dioxide that collects in the anatomic and physiologic dead space areas at the end of exhalation. Carbon dioxide is washed out and replaced by oxygen enriched gas that will be available to functioning alveoli on the next breath.

Additional flow provided by the invention during exhalation allows the self-breathing patient more effective and efficient use of the expiratory muscles, vocal cords, pharynx and lips to facilitate normal quality, non-fatiguing speech. Similarly, additional flow provided by the invention during exhalation allows the self-breathing patient to increase cough effectiveness by increasing flow during the expulsive phase of cough. Additional flow provided by the invention during exhalation allows the self-breathing patient more effective and efficient use of the vocal cords and lips in maximizing the physiologic effects related to the rate at which gas exits the chest. Different flow rates and flow patterns administered during the expiratory phase that are illustrated in the following examples may also result in these benefits in a variety of patient populations.

Figure 26:
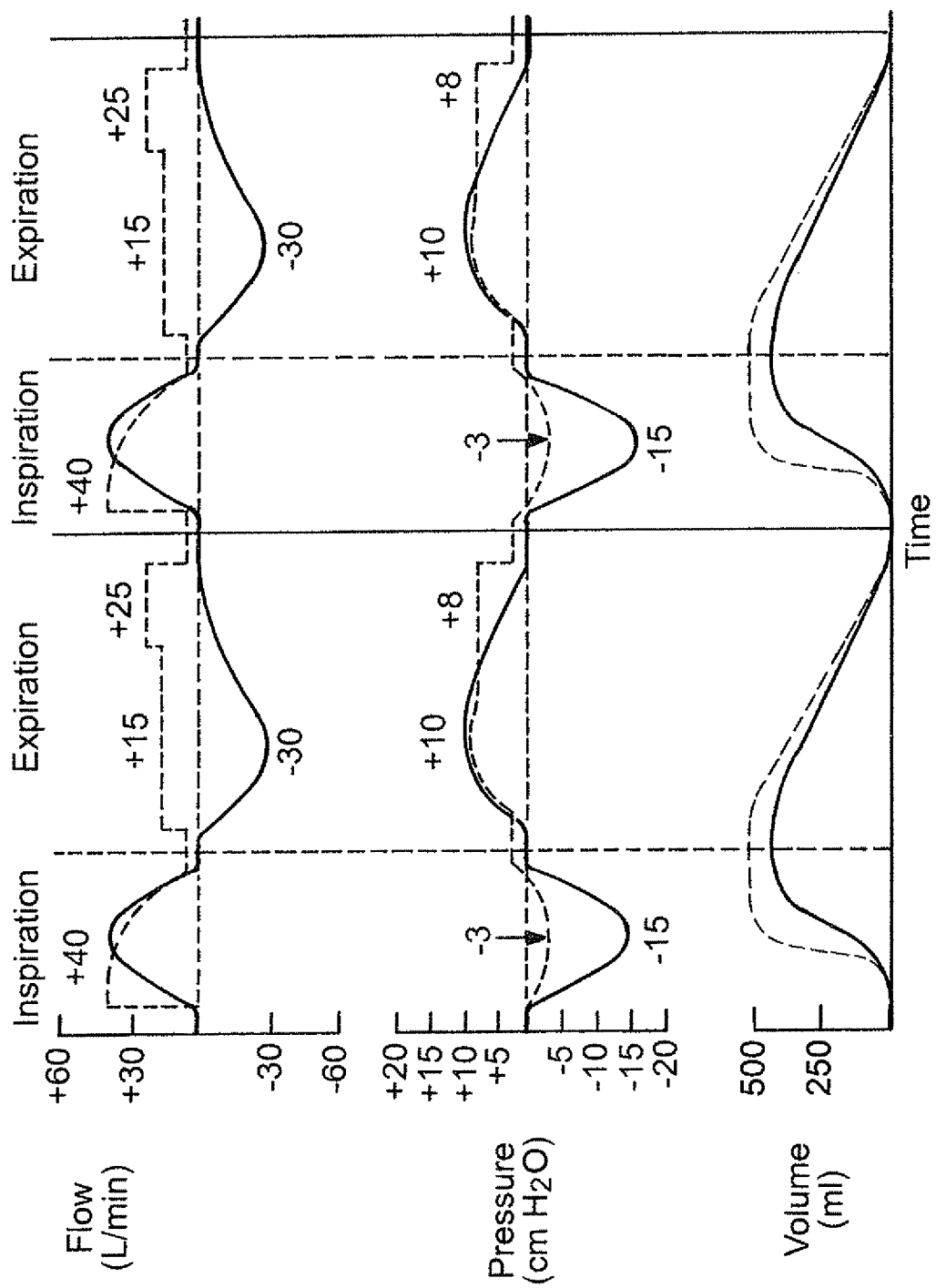
FIG. 26 is a set of graphs illustrating breathing in an emphysema patient in respiratory distress treated using the present system with an alternative waveform to deliver continuous flow-targeted ventilation.

FIG. 26 illustrates negative-pressure self-breathing in an emphysema patient in respiratory distress treated using the present system to deliver continuous flow-targeted ventilation (Example 2). The only difference in application of the invention between the patient management in FIG. 25 versus FIG. 26 is that the flow is not interrupted during the transition between exhalation and inhalation or in the transition between inhalation and exhalation. Based upon a patient-specific condition for a variety of disorders, continuous flow may or may not be advantageous. Continuous flow may also be used with any of the examples demonstrating interrupted flow.

Figure 27:
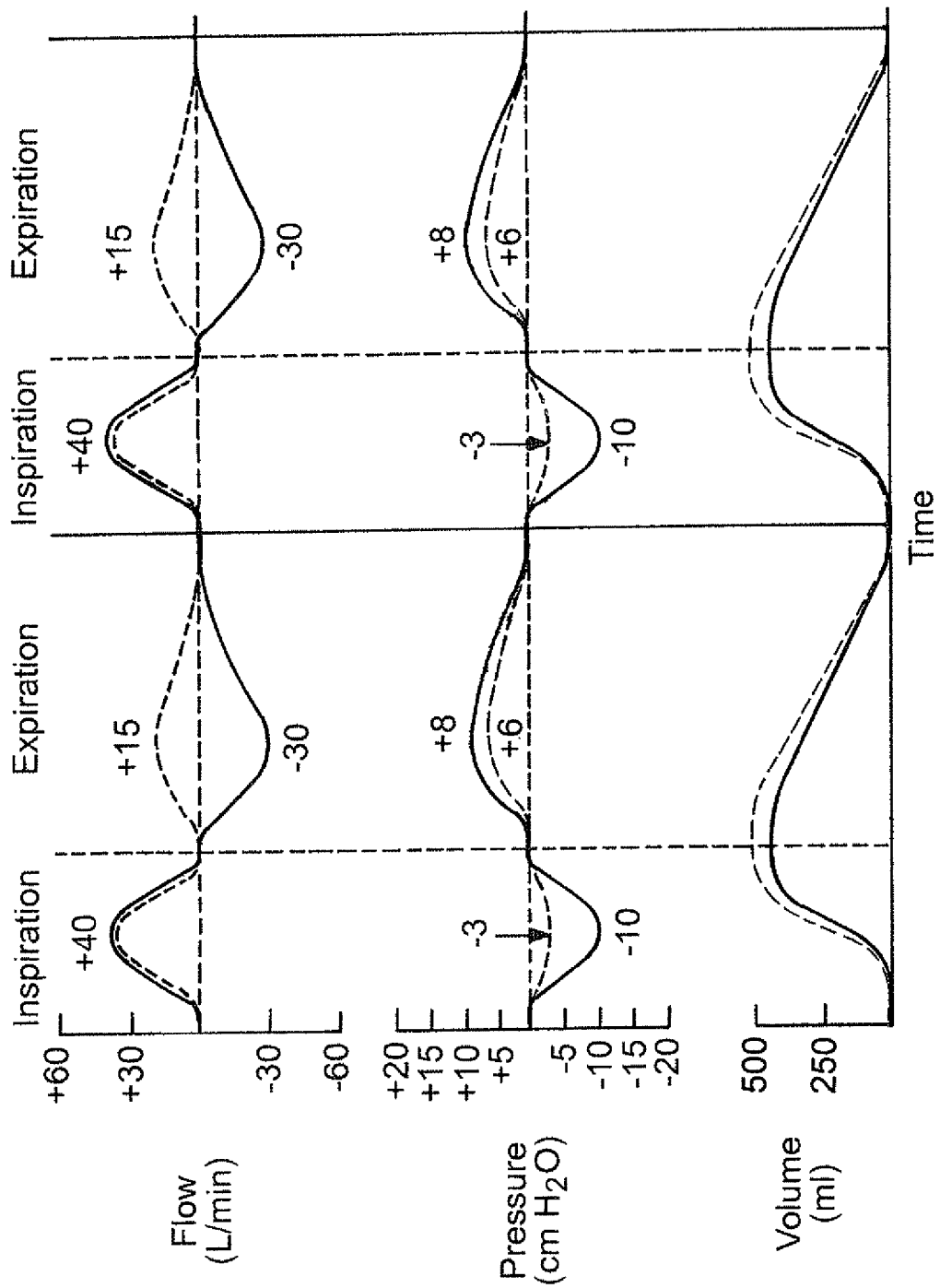
FIG. 27 is a set of graphs illustrating breathing in an emphysema patient in mild respiratory distress treated using the present invention to deliver with interrupted flow-targeted ventilation.

FIG. 27 illustrates negative-pressure self-breathing in an emphysema patient in mild respiratory distress treated using the present invention to deliver interrupted flow-targeted ventilation (Example 3). In this example of the implementation of the invention the patient is determined by the physician to be less compromised and requires less aggressive support. The application delivers a peak flow and flow pattern to mimic the sinusoidal inspiratory and expiratory flow patterns of the self-breathing patient. Reduced WOB on inspiration and expiration occur, alveolar ventilation is supported, and airway collapse is treated. Similarly, this flow-targeted ventilation with this flow pattern is likely to be beneficial for self-breathing patients with neurologic or neuromuscular diseases. The physiologic derangements in this patient population have been previously described. These individuals should benefit from the present invention.

Figure 28:
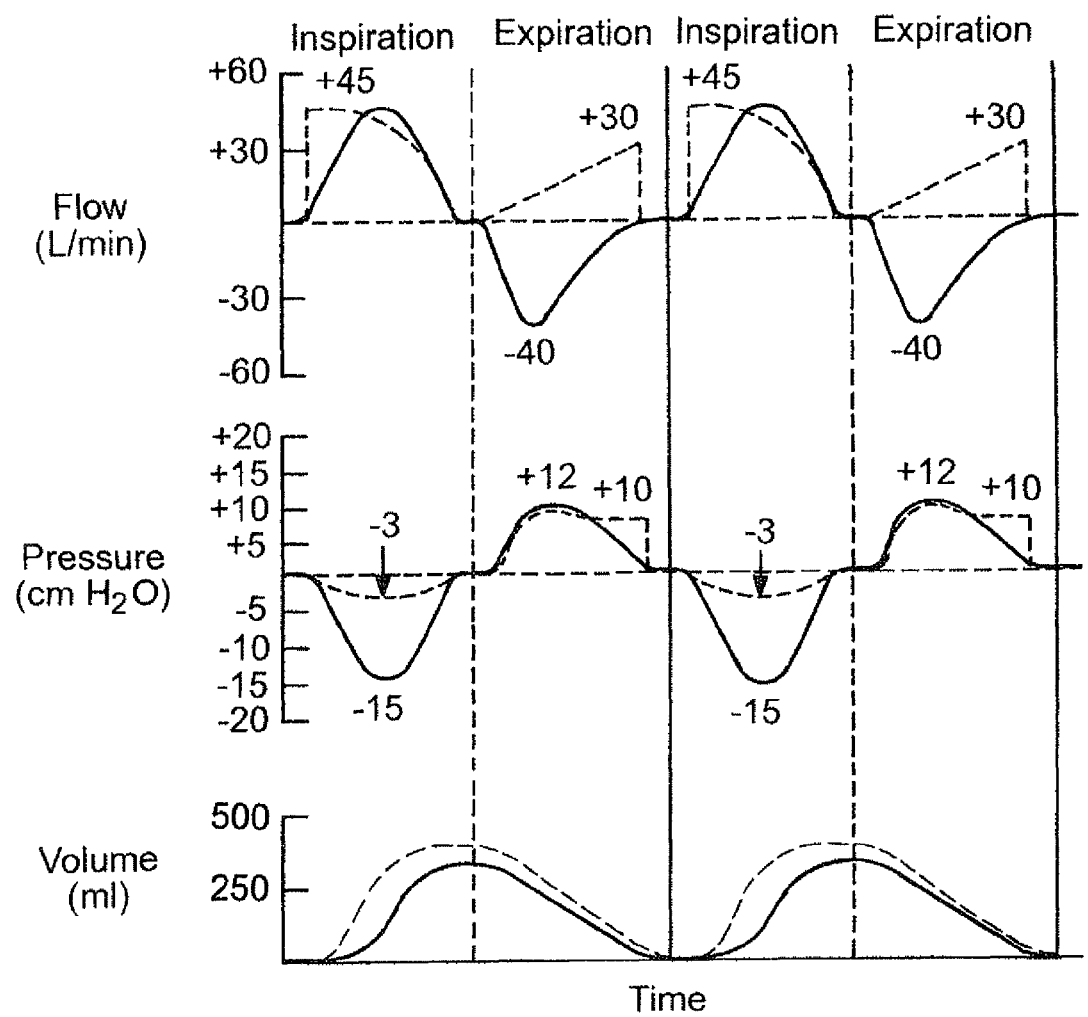
FIG. 28 is a set of graphs depicting breathing in an ARDS patient in respiratory distress treated with the present system to provide interrupted flow-targeted ventilation.

FIG. 28 depicts negative-pressure self-breathing in an ARDS patient in respiratory distress treated with the present system to provide interrupted flow-targeted ventilation (Example 4). FIG. 28 shows a rapidly accelerating inspiratory flow (with a peak of 45 cm $H_2O$ in this example). The initial accelerated flow is synchronized with the patient's initial inspiratory effort in the very first component of the inspiratory phase. The early onset of a high flow that exceeds requirements of the normal breathing pattern facilitates delivery of gas deep into functional alveolar gas exchange units, which results in improved ventilation to alveolar sacs causing improved oxygen uptake and carbon dioxide elimination. Flow during the very early component of the inspiratory phase has maximum impact upon oxygen delivery during self-breathing. Failure of adequate uptake of oxygen in spite of administration of a gas with a high percentage of oxygen (refractory hypoxemia) is a derangement in ARDS that should be improved by the present invention, particularly with this flow pattern that is also designed to recruit collapsed alveolar sacs. Following the accelerated inspiratory flow during the early inspiratory phase, the pattern transforms into a convex decelerating pattern that overlays sinusoidal flow pattern of the patient's breath during mid to late inspiration. The rapidly accelerating peak inspiratory flow and flow pattern reduces inspiratory WOB because the device delivers flow on the leading edge of the breath and less respiratory muscular work is required to physically draw the gas deep into the lungs. The first portion of the inspiratory phase in ARDS requires the most WOB because the stiff lungs characteristic of this disorder are most stiff (highest elastic recoil) at lowest lung volumes encountered at the beginning of inspiration. FIG. 28 demonstrates a reduction in the inspiratory negative pressure swing, which indicates reduced inspiratory WOB. In other words, the negative pressure required by the patient to inspire is mitigated by use of the device's targeted flow pattern. Because of the open design of the system, positive pressure during inspiration does not occur because any gas that is not inhaled can easily escape into the atmosphere, mitigating positive pressure buildup.

Patients with ARDS, due to the high elastic recoil created by the disorder, are generally able to passively exhale gas from the lungs. However, with the tendency of alveolar sacs to collapse, administration of flow during exhalation can be beneficial in preventing further atelectasis (alveolar collapse) or even opening collapsed alveolar sacs (recruitment). The ARDS patient requires a high minute ventilation. Though excessive physiologic dead space may not be present, any reduction in physiologic and/or anatomic dead space can reduce ventilatory requirements during self-breathing. The elevated flow achieved at end-expiration with this flow-targeted pattern is designed to meet those needs through carbon dioxide wash out.

Figure 29:
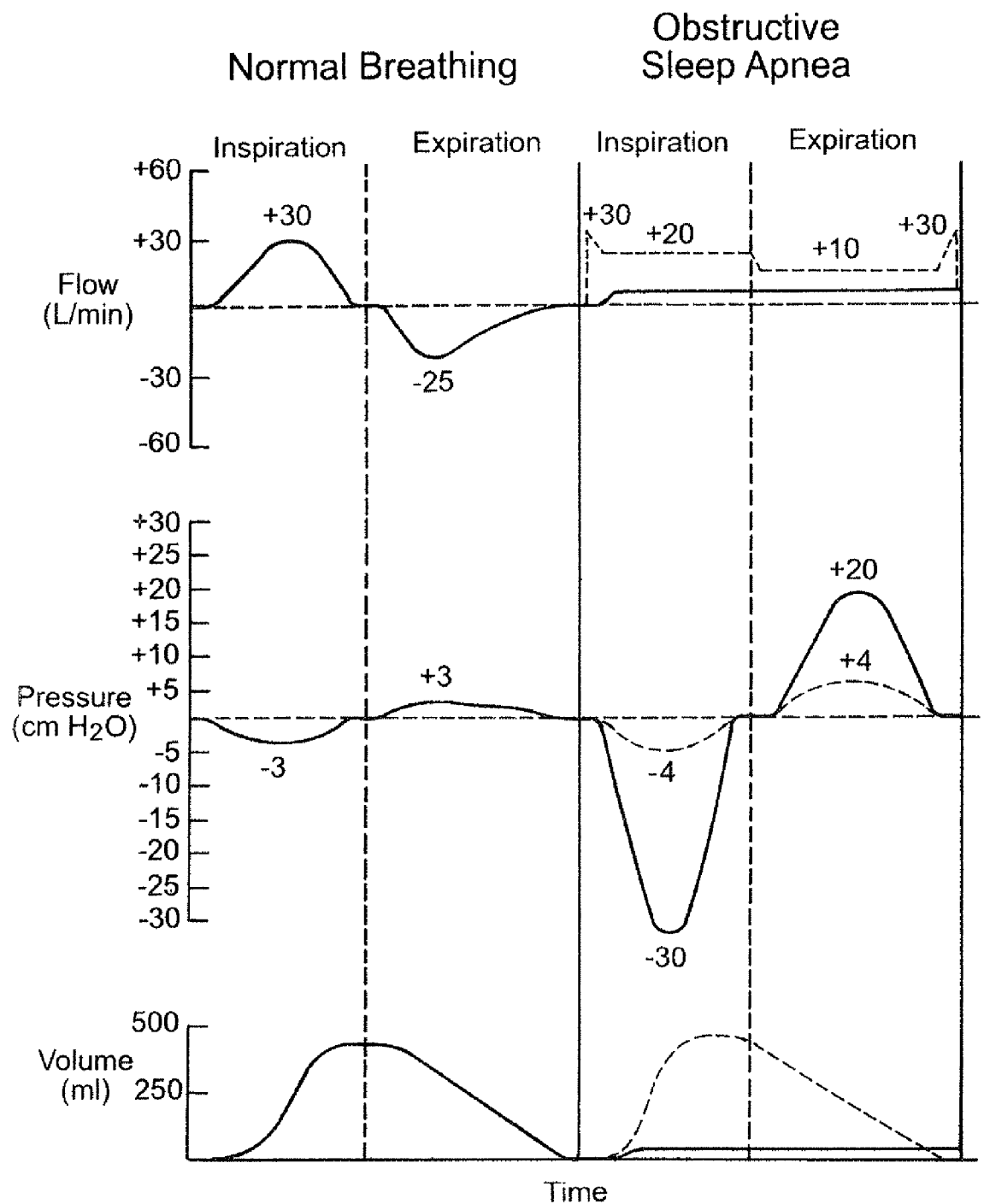
FIG. 29 illustrates breathing in an obstructive sleep apnea patient in respiratory distress treated with the present system.

FIG. 29 (Example 5) illustrates negative-pressure self-breathing in an obstructive sleep apnea patient in respiratory distress treated with the present system. Upper airway collapse and the physiologic derangements in obstructive sleep apnea have been previously described. In the treatment of obstructive sleep apnea, the present system can be used to target a flow pattern with flow rates that maintain patency or openness of the upper airway during self-breathing. The flow rate (and pattern) required to achieve and maintain patency or openness may be different relative to the phase or component of the phase of the respiratory cycle and requirements may vary from individual to individual.

FIG. 29 illustrates an example where an initial high flow at the onset of inspiration occurs to prevent upper airway collapse during the initial negative pressure generated at the onset of inspiration. Though the flow pattern tapers during mid to late inspiration, relatively high flows are maintained to prevent inspiratory upper airway collapse, which results in increase inspiratory WOB. The mitigation of increased inspiratory negative pressures prevents obstruction from begetting obstruction. Similarly, relatively high flows are maintained during the expiratory phase though flows are of less magnitude. These flows also stent the airway during exhalation and prevent the floppy upper airway tissues from causing obstruction. Accelerated flow occurs towards the end of exhalation in order to maintain patency prior to the onset of the next negative pressure swing at the onset of inspiration. This is an example where continuous flow, rather than interrupted flow, may be the preferred method as it may be more effective in preventing upper airway collapse in obstructive sleep apnea. Unlike Bi-level Positive Pressure Ventilation or Continuous Positive Airway Pressure (SCSPPV systems) a partial obstruction between the upper airway and atmosphere is not required. Patients self-breathe with an open system. Complications and discomforts of SCSPPV systems are avoided. Relief and prevention of obstruction prevents the physiologic derangements associated with the disorder. For patients with central sleep apnea, flow patterns shown in FIGS. 25 and 26 should be effective in improving the physiologic derangements.

Figure 30:
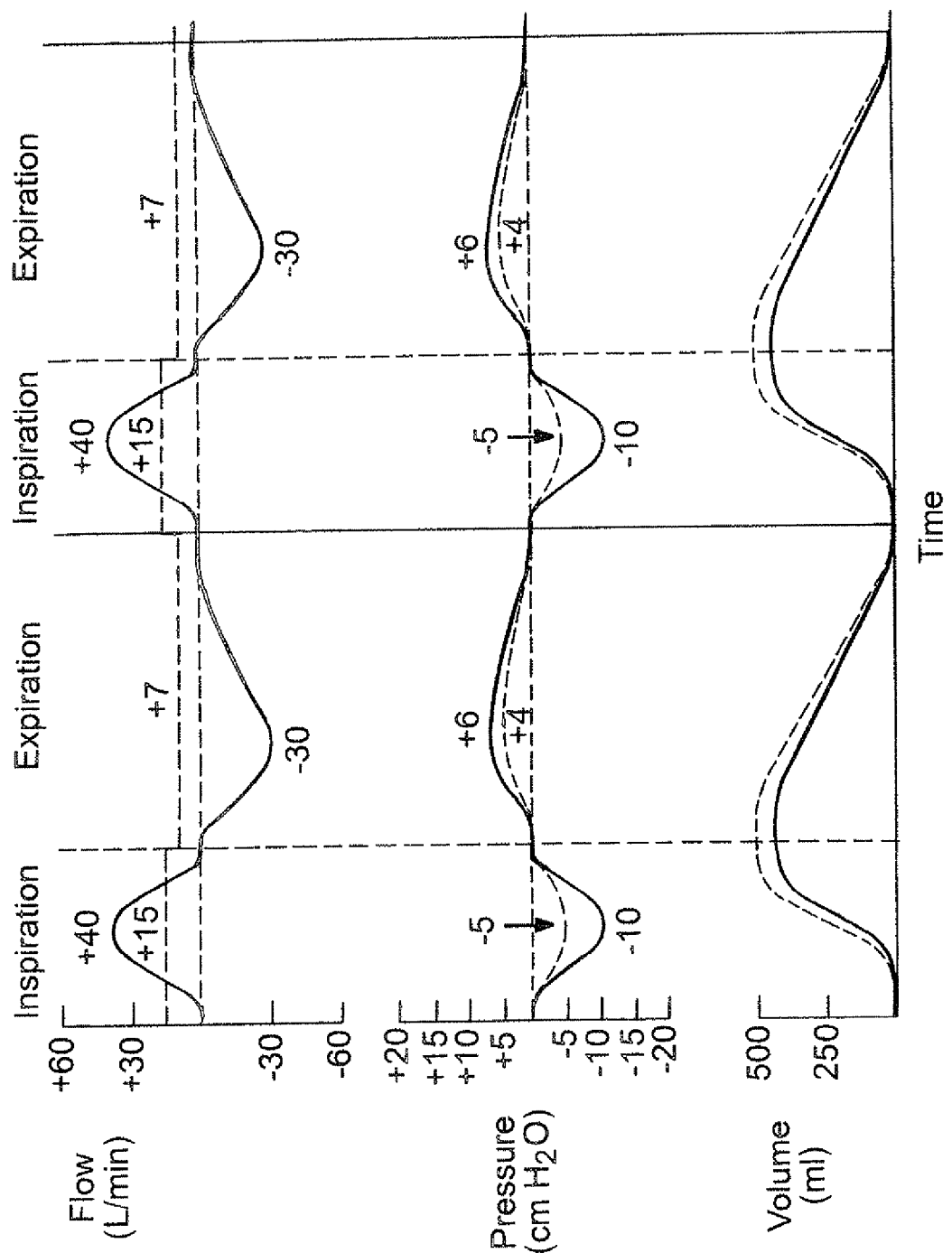
FIG. 30 illustrates breathing in an emphysema patient in mild respiratory distress treated using the present system with another alternative waveform to deliver uninterrupted flow-targeted ventilation.

FIG. 30 (Example 6) illustrates negative-pressure self-breathing in an emphysema patient in mild respiratory distress treated using the present system to deliver uninterrupted flow-targeted ventilation. In this example of an implementation of the invention, the patient is also determined by the physician to be less compromised and requires less aggressive support. However, the support is designed to augment self-breathing. A flow of 15 L/min is selected to be administered throughout the inspiratory phase and a flow of 7 L/min is selected to be administered throughout the expiratory phase. Thus, flow-targeted ventilation is synchronized with the respiratory cycle and results in a flow pattern that is not the same constant flow throughout the entire respiratory cycle. The higher inspiratory flow is designed to augment the inspiratory breath and the lower expiratory flow is designed to facilitate speech and glottic functioning and to prevent airway collapse and wash out dead space without providing excessive expiratory flows for this particular patient. Flow is uninterrupted during transitions between inspiration and expiration and between expiration and inspiration.

Figure 31:
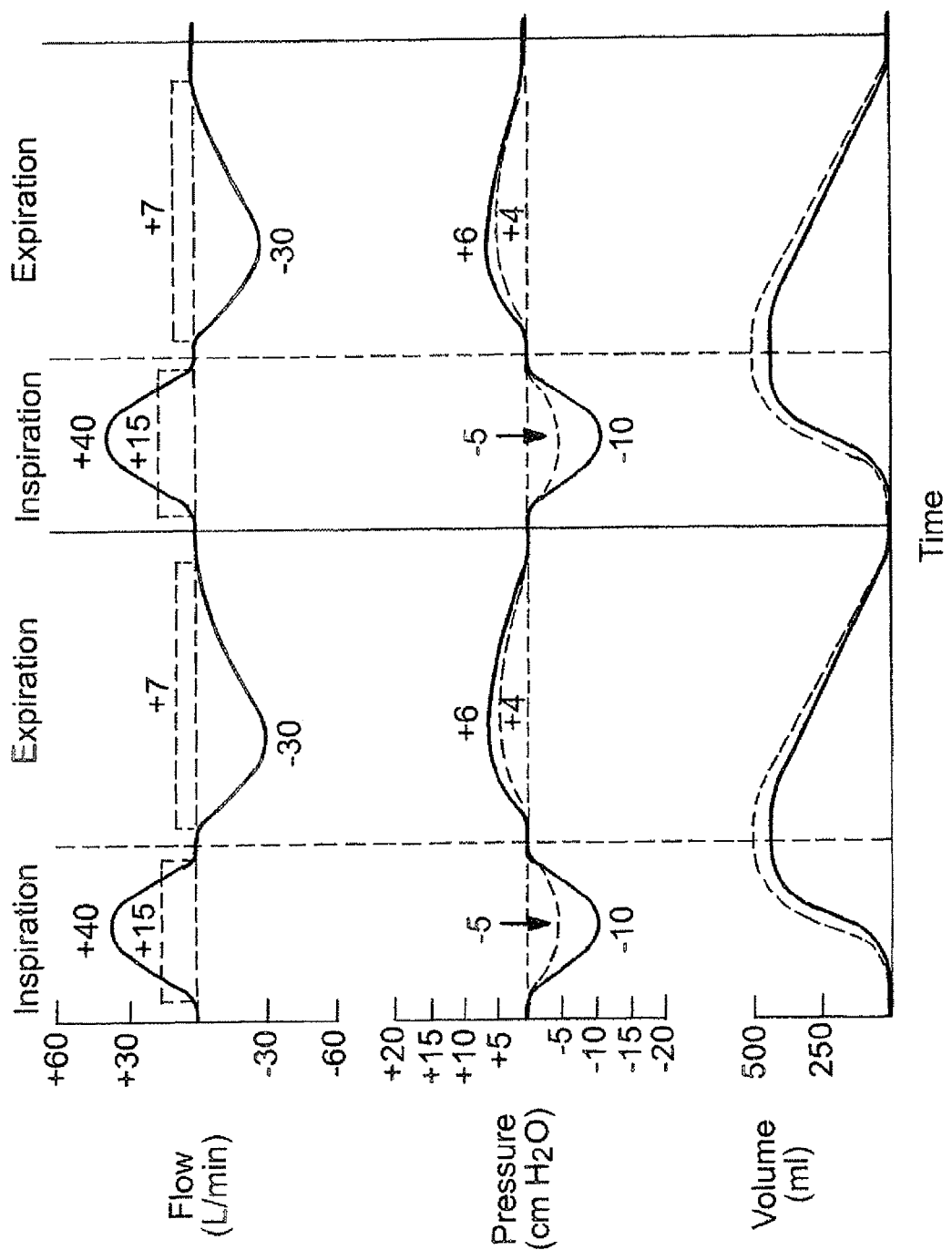
FIG. 31 illustrates breathing in an emphysema patient in mild respiratory distress treated with the present invention supplying interrupted flow-targeted ventilation with modification of the alternative waveform of FIG. 30.

FIG. 31 illustrates negative-pressure self-breathing in an emphysema patient in mild respiratory distress treated with the present invention supplying interrupted flow-targeted ventilation (Example 7). Similar to the example in FIG. 30 with the implementation of the invention, the patient is also determined by the physician to be less compromised and requires less aggressive support. However, the support is designed to augment self-breathing. A flow of 15 L/min is selected to be administered throughout the inspiratory phase and a flow of 7 L/min is selected to be administered throughout the expiratory phase. Thus, flow-targeted ventilation is synchronized with the respiratory cycle and results in a flow pattern that is not constant throughout the entire respiratory cycle. The higher inspiratory flow is designed to augment the inspiratory breath and the lower expiratory flow is designed to facilitate speech and glottic functioning, to prevent airway collapse and wash out dead space without providing excessive expiratory flows for this particular patient. The difference is that flow is interrupted during transitions between inspiration and expiration and between expiration and inspiration.

Figure 32:
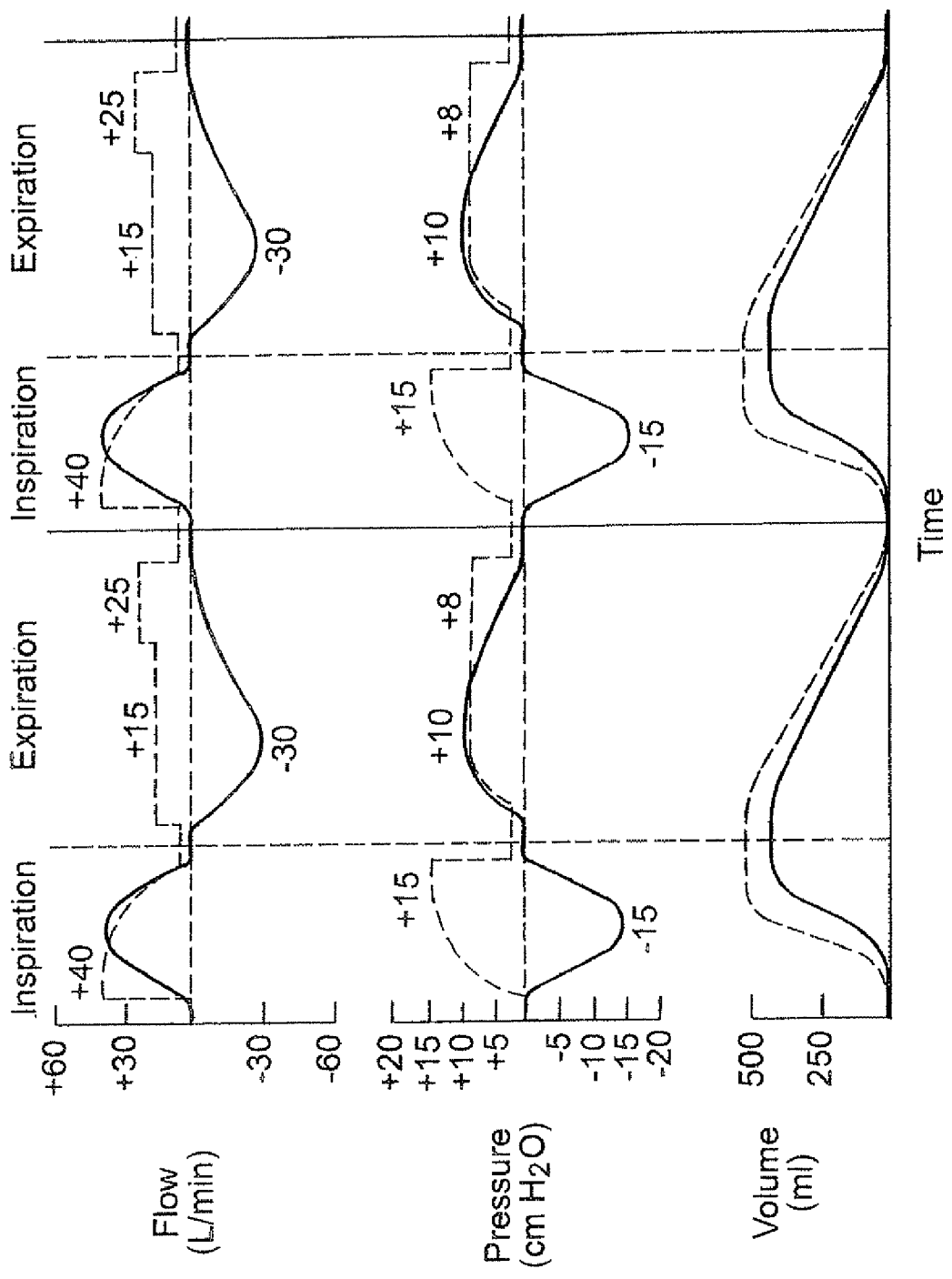
FIG. 32 illustrates breathing in an emphysema patient in mild respiratory distress treated using the present invention with continuous flow-targeted ventilation and patient control of passive inflation.

FIG. 32 illustrates negative-pressure self-breathing in an emphysema patient in mild respiratory distress treated using the present invention with continuous flow-targeted ventilation and patient control of passive inflation (Example 8). As noted previously, patients with lung disease may use their vocal cords to control or regulate flow in and out of the lungs. Additionally, patients may also "purse" or close their lips to control respiratory flow. This requires little effort. Certain patients may benefit if they learn to close their vocal cords and purse their lips on inspiration, and rather than using negative pressure generated through WOB by the respiratory muscles, they would allow the flow of gas from the present system to passively and effortlessly inflate the lungs. Unlike CSPPV where the device determines when the breath is triggered on or inspiration is cycled off, the self-breathing patient controls the respiratory cycle.

FIG. 32 demonstrates an emphysema patient in respiratory distress where, due to closure of the vocal cords or mouth on inspiration, the flow from the device passively inflates the lungs. Negative pressure otherwise required to inflate the lungs by the self-breathing patient's respiratory muscles is mitigated. The flow pattern is similar to FIG. 26 where the fast ramp-up allows the patient to promptly inflate the lungs, allowing more time for exhalation. Adequate time to exhale is beneficial. Little or no work is required by the diaphragm or other inspiratory muscles. Though positive pressure is achieved on inspiration, no pressure delivered by the device is targeted and the patient determines when the pressure is relieved by opening the vocal cords and lips. Partial closure of the lips and vocal cords during the expiratory phase and resulting physiologic benefits have been described. Other targeted inspiratory flows and flow patterns may be beneficial in this patient population.

The above disclosure sets forth a number of embodiments of the present invention described in detail with respect to the accompanying drawings. Those skilled in this art will appreciate that various changes, modifications, other structural arrangements, and other embodiments could be practiced under the teachings of the present invention without departing from the scope of this invention as set forth in the following claims.

We claim:

1. An apparatus for delivering a flow of oxygen-containing gas to the airway of a spontaneously-breathing patient, said apparatus comprising:
   a nasal tube delivering a flow of oxygen-containing gas into a patient's airway without interfering with a patient's spontaneous respiration;
   a gas source delivering a variable flow of oxygen-containing gas through the nasal tube;
   a sensor detecting a physical property of a patient's respiratory cycle; and
   a processor monitoring the sensor and controlling the gas source to deliver a flow of oxygen-containing gas through the nasal tube to augment the patient's spontaneous respiration, said flow varying over each inspiratory and expiratory phase of the respiratory cycle in a predetermined non-constant flow waveform synchronized with the respiratory cycle, said waveform including:
   (a) a positive flow accelerating at the onset of the patient's inspiratory phase at a flow rate sufficient to significantly mitigate the airway pressure the patient must generate during spontaneous breathing and thereby reduce the patient's work of breathing; and
   (b) a positive flow during at least the early portion of the patient's expiratory phase at a flow rate sufficient to significantly mitigate the airway pressure the patient must generate during spontaneous breathing and thereby reduce the patient's work of breathing, and to wash carbon dioxide from the patient's airway.

2. The apparatus of claim 1 wherein the sensor is attached to a portion of the nasal tube in a patient's airway.

3. The apparatus of claim 1 further comprising a sampling tube extending along a portion of the nasal tube in a patient's airway to the sensor.

4. The apparatus of claim 1 wherein the sensor comprises a pressure transducer.

5. The apparatus of claim 1 wherein the sensor comprises a flow sensor.

6. The apparatus of claim 1 wherein the sensor comprises a thermistor.

7. The apparatus of claim 1 wherein the sensor comprises a carbon dioxide sensor.

8. The apparatus of claim 1 wherein the nasal tube comprises a nasopharyngeal catheter.

9. The apparatus of claim 1 wherein the nasal tube comprises a nasal cannula.

10. The apparatus of claim 1 wherein the processor interrupts the flow for a portion of the respiratory cycle.

11. An apparatus for delivering a flow of oxygen-containing gas to the airway of a spontaneously-breathing patient, said apparatus comprising:
   a nasal tube delivering a flow of oxygen-containing gas into a patient's airway without interfering with a patient's spontaneous respiration;
   a gas source delivering a variable flow of oxygen-containing gas through the nasal tube;
   a sensor attached to a portion of the nasal tube in a patient's airway for detecting a physical property of a patient's respiratory cycle; and
   a processor monitoring the sensor and controlling the gas source to deliver a flow of oxygen-containing gas through the nasal tube to augment the patient's spontaneous respiration, said flow varying over each inspiratory and expiratory phase of the respiratory cycle in a predetermined non-constant flow waveform synchronized with the respiratory cycle, said waveform including:
   (a) a positive flow accelerating at the onset of the patient's inspiratory phase at a flow rate sufficient to significantly mitigate the airway pressure the patient must generate during spontaneous breathing and thereby reduce the patient's work of breathing; and
   (b) a positive flow during at least the early portion of the patient's expiratory phase at a flow rate sufficient to significantly mitigate the airway pressure the patient must generate during spontaneous breathing and thereby reduce the patient's work of breathing, and to wash carbon dioxide from the patient's airway.

12. The apparatus of claim 11 wherein the sensor comprises a flow sensor.

13. The apparatus of claim 11 wherein the sensor comprises a thermistor.

14. The apparatus of claim 11 wherein the nasal tube comprises a nasopharyngeal catheter.

15. The apparatus of claim 11 wherein the nasal tube comprises a nasal cannula.

16. The apparatus of claim 11 wherein the processor interrupts the flow for a portion of the respiratory cycle.

17. An apparatus for delivering a flow of oxygen-containing gas to the airway of a spontaneously-breathing patient, said apparatus comprising:
   a nasal tube delivering a flow of oxygen-containing gas into a patient's airway without interfering with a patient's spontaneous respiration;
   a gas source delivering a variable flow of oxygen-containing gas through the nasal tube;
   a sensor for detecting a physical property of a patient's respiratory cycle;
   a sampling tube extending along at least a portion of the nasal tube into a patient's airway to the sensor; and
   a processor monitoring the sensor and controlling the gas source to deliver a flow of oxygen-containing gas through the nasal tube to augment the patient's spontaneous respiration, said flow varying over each inspiratory and expiratory phase of the respiratory cycle in a predetermined non-constant flow waveform synchronized with the respiratory cycle, said waveform including:
   (a) a positive flow accelerating at the onset of the patient's inspiratory phase at a flow rate sufficient to significantly mitigate the airway pressure the patient must generate during spontaneous breathing and thereby reduce the patient's work of breathing; and
   (b) a positive flow during at least the early portion of the patient's expiratory phase at a flow rate sufficient to significantly mitigate the airway pressure the patient must generate during spontaneous breathing and thereby reduce the patient's work of breathing, and to wash carbon dioxide from the patient's airway.

18. The apparatus of claim 17 wherein the sensor comprises a pressure transducer.

19. The apparatus of claim 17 wherein the sensor comprises a carbon dioxide sensor.

20. The apparatus of claim 17 wherein the sensor comprises a flow sensor.

21. The apparatus of claim 17 wherein the nasal tube comprises a nasopharyngeal catheter.

22. The apparatus of claim 17 wherein the nasal tube comprises a nasal cannula.

* * * * *